United States Patent
Ledeboer et al.

(10) Patent No.: US 8,633,205 B2
(45) Date of Patent: Jan. 21, 2014

(54) SUBSTITUTED PYRROLO[2,3-D]PYRIMIDINES AS INHIBITORS OF PROTEIN KINASES

(75) Inventors: Mark Ledeboer, Acton, MA (US); Albert Pierce, Cambridge, MA (US); Guy Bemis, Arlington, MA (US); Luc Farmer, Foxboro, MA (US); Tiansheng Wang, Concord, MA (US); David Messersmith, Somerville, MA (US); John Duffy, Northborough, MA (US); Francesco Salituro, Marlboro, MA (US); Jian Wang, Newton, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 870 days.

(21) Appl. No.: 11/346,048

(22) Filed: Feb. 2, 2006

(65) Prior Publication Data

US 2006/0183761 A1  Aug. 17, 2006
US 2007/0004762 A9  Jan. 4, 2007

Related U.S. Application Data

(60) Provisional application No. 60/649,781, filed on Feb. 3, 2005.

(51) Int. Cl.
| | |
|---|---|
| *C07D 487/04* | (2006.01) |
| *A61K 31/519* | (2006.01) |
| *A61K 31/497* | (2006.01) |
| *A61P 35/00* | (2006.01) |
| *A61P 37/06* | (2006.01) |
| *A61P 25/28* | (2006.01) |

(52) U.S. Cl.
USPC ............ 514/265.1; 544/280; 514/252.16

(58) Field of Classification Search
USPC ............ 544/281, 280; 514/252.16, 265.1
See application file for complete search history.

(56) References Cited

U.S. PATENT DOCUMENTS 7,253,286 B2 *  8/2007  Funahashi et al. ............ 546/153

FOREIGN PATENT DOCUMENTS

| EP | 795556 A1 * | 9/1997 |
| WO | WO 01/42246 A2 | 6/2001 |

OTHER PUBLICATIONS

Arcadi et. al. (Synlett, 1991, 6, 409-411), see STN printout.*
Yamamoto et. al. (Bull. Chem. Soc., 1977, 50(2), 453-458), see STN printout.*
Khachatryan, V.E. "Synthesis and mass spectra of some furo-, thieno-, and pyrrolo[2,3-d]pyrimidines", Database CAPLUS, accession No. 1989:135185, CAPLUS RN 11907-35-6, downloaded Jun. 6, 2006.
Yamamoto et al. "Seven-membered N-heterocycles", Database CAPLUS, accession No. 1977:439400, CAPLUS RN 63205-44-7, downloaded Jun. 6, 2006.

* cited by examiner

*Primary Examiner* — Susanna Moore
(74) *Attorney, Agent, or Firm* — Lisa A. Dixon; Susan C. Kelly

(57) ABSTRACT

The present invention relates to compounds of the following formula:

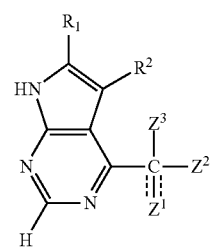

which are useful as inhibitors of protein kinases. The invention also provides pharmaceutically acceptable compositions comprising said compounds and methods of using the compositions in the treatment of various disease, conditions, or disorders.

6 Claims, No Drawings

SUBSTITUTED PYRROLO[2,3-D]PYRIMIDINES AS INHIBITORS OF PROTEIN KINASES

This application claims the benefit of U.S. Provisional Application 60/649,781, filed Feb. 3, 2005, which is herein incorporated by reference in its entirety.

TECHNICAL FIELD OF THE INVENTION

The present invention relates to compounds useful as inhibitors of Janus kinases (JAK). The invention also provides pharmaceutically acceptable compositions comprising the compounds of the invention and methods of using the compositions in the treatment of various disorders.

BACKGROUND OF THE INVENTION

The Janus kinases (JAK) are a family of tyrosine kinases consisting of JAK1, JAK2, JAK3 and TYK2. The JAKs play a critical role in cytokine signaling. The down-stream substrates of the JAK family of kinases include the signal transducer and activator of transcription (STAT) proteins. JAK/STAT signaling has been implicated in the mediation of many abnormal immune responses such as allergies, asthma, autoimmune diseases such as transplant rejection, rheumatoid arthritis, amyotrophic lateral sclerosis and multiple sclerosis as well as in solid and hematologic malignancies such as leukemias and lymphomas. JAK2 has also been implicated in myeloproliferative disorders, which include polycythemia vera, essential thrombocythemia, chronic idiopathic myelofibrosis, myeloid metaplasia with myelofibrosis, chronic myeloid leukemia, chronic myelomonocytic leukemia, chronic eosinophilic leukemia, hypereosinophilic syndrome and systematic mast cell disease.

The Rho-associated coiled-coil forming protein serine/threonine kinase (ROCK) family are effectors of Ras-related small GTPase Rho. The ROCK family includes p160ROCK (ROCK-1), ROKα/Rho-kinase/ROCK-II, protein kinase PKN, and citron and citron kinase. ROCK has been implicated in various diseases and disorders including hypertension, chronic obstructive pulmonary disease, cerebral vasospasm, coronary vasospasm, bronchial asthma, erectile dysfunction, glaucoma, vascular smooth muscle cell proliferation, myocardial hypertrophy, malignoma, ischemia/reperfusion-induced injury, endothelial dysfunction, Crohn's Disease and colitis, neurite outgrowth, Raynaud's Disease, angina, Alzheimer's disease, atherosclerosis, and cardiac hypertrophy and perivascular fibrosis.

Protein kinase A (PKA; also known as cAMP-dependent protein kinase) is a tetrameric holoenzyme, which contains two catalytic subunits bound to a homo-dimeric regulatory subunit (which acts to inhibit the catalytic sub-units). On binding of cAMP (enzyme activation), the catalytic subunits dissociate from the regulatory subunits to yield the active serine/threonine kinase. Three isoforms of the catalytic sub-unit (C-α, C-β and C-γ) have been reported to date, with the C-α subunit being the most extensively studied, primarily because of its elevated expression in primary and metastatic melanomas. PKA has been shown to regulate many vital functions including energy metabolism, gene transcription, proliferation, differentiation, reproductive function, secretion, neuronal activity, memory, contractility and motility.

Accordingly, there is a great need to develop compounds useful as inhibitors of protein kinases, including JAK family, ROCK and PKA kinases. In particular, it would be desirable to develop compounds that are useful as inhibitors of JAK2 and JAK3.

SUMMARY OF THE INVENTION

It has now been found that compounds of this invention, and pharmaceutically acceptable compositions thereof, are effective as inhibitors of protein kinases, particularly the JAK family kinases. In certain embodiments, these compounds are effective as inhibitors of JAK3 protein kinases. These compounds have the general formula I:

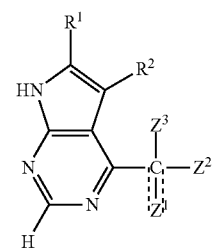

or a pharmaceutically acceptable salt thereof, wherein $R^1$, $R^2$, $Z^1$, $Z^2$, and $Z^3$ are as defined below.

These compounds, and pharmaceutically acceptable compositions thereof, are useful for treating or lessening the severity of a variety of disorders, including allergic disorders such as asthma and atopic dermatitis, autoimmune diseases such as SLE lupus and psoriasis, conditions associated with organ transplantation, myeloproliferative disorders, hypertension, chronic obstructive pulmonary disease and proliferative disorders such as melanoma.

DETAILED DESCRIPTION OF THE INVENTION

Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position.

As described herein, when the term "optionally substituted" precedes a list, said term refers to all of the subsequent substitutable groups in that list. For example, if X is halogen; optionally substituted $C_{1-3}$alkyl or phenyl; X may be either optionally substituted alkyl or optionally substituted phenyl. Likewise, if the term "optionally substituted" follows a list, said term also refers to all of the substitutable groups in the prior list unless otherwise indicated. For example: if X is halogen, $C_{1-3}$alkyl or phenyl wherein X is optionally substituted by $J^X$, then both $C_{1-3}$alkyl and phenyl may be optionally substituted by $J^X$. As is apparent to one having ordinary skill in the art, groups such as H, halogen, $NO_2$, CN, $NH_2$, OH, or $OCF_3$ would not be included because they are not substitutable groups.

Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As described herein, a bond drawn from a substituent to the center of one ring within a multiple-ring system (as shown below), represents substitution of the substituent at any substitutable position in any of the rings within the multiple ring system. For example, Figure a represents possible substitution in any of the positions shown in Figure b.

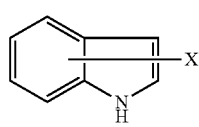

Figure a

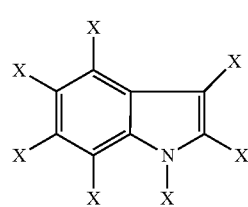

Figure b

This also applies to multiple ring systems fused to optional ring systems (which would be represented by dotted lines). For example, in Figure c, X is an optional substituent both for ring A and ring B.

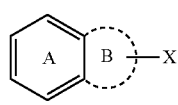

Figure c

If, however, two rings in a multiple ring system each have different substituents drawn from the center of each ring, then, unless otherwise specified, each substituent only represents substitution on the ring to which it is attached. For example, in Figure d, Y is an optionally substituent for ring A only, and X is an optional substituent for ring B only.

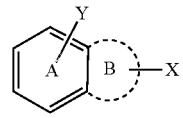

Figure d

The term "aliphatic" or "aliphatic group", as used herein, means a straight-chain (i.e., unbranched) or branched, substituted or unsubstituted hydrocarbon chain that is completely saturated or that contains one or more units of unsaturation. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Suitable aliphatic groups include, but are not limited to, linear or branched, substituted or unsubstituted alkyl, alkenyl, or alkynyl groups. Further examples of aliphatic groups include methyl, ethyl, propyl, butyl, isopropyl, isobutyl, vinyl, and sec-butyl.

The term "cycloaliphatic" (or "carbocycle" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable cycloaliphatic groups include, but are not limited to, cycloalkyl, cycloalkenyl, and cycloalkynyl. Further examples of aliphatic groups include cyclopentyl, cyclopentenyl, cyclohexyl, cyclohexenyl, cycloheptyl, and cycloheptenyl.

The term "heterocycle", "heterocyclyl", "heterocycloaliphatic", or "heterocyclic" as used herein means nonaromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

Further examples of heterocyclic rings include, but are not limited to, the following monocycles: 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl; 2-imidazolidinyl, 4-imidazolidinyl, 5-imidazolidinyl, and the following bicycles: 3-1H-benzimidazol-2-one, 3-(1-alkyl)-benzimidazol-2-one, indolinyl, tetrahydroquinolinyl, tetrahydroisoquinolinyl, benzothiolane, benzodithiane, and 1,3-dihydro-imidazol-2-one.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined herein below. Examples of aryl rings would include phenyl, naphthyl, and the heteroaryl group listed below.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

Further examples of heteroaryl rings include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

An aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from those listed in the definition of $J^X$, $J^Q$, $J^R$ above; halogen; —R$^\circ$; —OR$^\circ$; —SR$^\circ$; 1,2-methylenedioxy; 1,2-ethylenedioxy; phenyl (Ph) optionally substituted with R$^\circ$; —O(Ph) optionally substituted with R$^\circ$; —(CH$_2$)$_{1-2}$(Ph), optionally substituted with R$^\circ$; —CH═CH(Ph), optionally substituted with R$^\circ$; —NO$_2$; —CN; —N(R$^\circ$)$_2$; —NR$^\circ$C(O)R$^\circ$; —NR$^\circ$C(S)R$^\circ$; —NR$^\circ$C(O)N(R$^\circ$)$_2$; —NR$^\circ$C(S)N(R$^\circ$)$_2$; —NR$^\circ$CO$_2$R$^\circ$; —NR$^\circ$NR$^\circ$C(O)R$^\circ$; —NR$^\circ$NR$^\circ$C(O)N(R$^\circ$)$_2$; —NR$^\circ$NR$^\circ$CO$_2$R$^\circ$; —C(O)C(O)R$^\circ$; —C(O)CH$_2$C(O)R$^\circ$; —CO$_2$R$^\circ$; —C(O)R$^\circ$; —C(S)R$^\circ$; —C(O)N(R$^\circ$)$_2$; —C(S)N(R$^\circ$)$_2$; —OC(O)N(R$^\circ$)$_2$; —OC(O)R$^\circ$; —C(O)N(OR$^\circ$)R$^\circ$; —C(NOR$^\circ$)R$^\circ$; —S(O)$_2$R$^\circ$; —S(O)$_3$R$^\circ$; —SO$_2$N(R$^\circ$)$_2$; —S(O)R$^\circ$; —NR$^\circ$SO$_2$N(R$^\circ$)$_2$; —NR$^\circ$SO$_2$R$^\circ$; —N(OR$^\circ$)R$^\circ$; —C(═NH)—N(R$^\circ$)$_2$; or —(CH$_2$)$_{0-2}$NHC(O)R$^\circ$ wherein each independent occurrence of R$^\circ$ is selected from hydrogen, optionally substituted C$_{1-6}$ aliphatic, an unsubstituted 5-6 membered heteroaryl or heterocyclic ring, phenyl, —O(Ph), or —CH$_2$(Ph), or, notwithstanding the definition above, two independent occurrences of R$^\circ$, on the same substituent or different substituents, taken together with the atom(s) to which each R$^\circ$ group is bound, form a 5-8-membered heterocyclyl, aryl, or heteroaryl ring or a 3-8-membered cycloalkyl ring having 0-3 heteroatoms independently selected from nitrogen, oxygen, or sulfur. Optional substituents on the aliphatic group of R$^\circ$ are selected from NH$_2$, NH(C$_{1-4}$aliphatic), N(C$_{1-4}$aliphatic)$_2$, halogen, C$_{1-4}$aliphatic, OH, O(C$_{1-4}$aliphatic), N$_2$, CN, CO$_2$H, CO$_2$(C$_{1-4}$aliphatic), O(halo C$_{1-4}$aliphatic), or haloC$_{1-4}$aliphatic, wherein each of the foregoing C$_{1-4}$aliphatic groups of R$^\circ$ is unsubstituted.

An aliphatic or heteroaliphatic group, or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: ═O, ═S, ═NNHR*, ═NN(R*)$_2$, ═NNHC(O)R*, ═NNHCO$_2$(alkyl), ═NNHSO$_2$(alkyl), or ═NR*, where each R* is independently selected from hydrogen or an optionally substituted C$_{1-6}$ aliphatic. Optional substituents on the aliphatic group of R* are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of the foregoing C$_{1-4}$aliphatic groups of R* is unsubstituted.

Optional substituents on the nitrogen of a non-aromatic heterocyclic ring include those listed in the definition of $J^Q$ and R$^7$ herein; —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(═S)N(R$^+$)$_2$, —C(═NH)—N(R$^+$)$_2$, or —NR$^+$SO$_2$R$^+$; wherein R$^+$ is hydrogen, an optionally substituted C$_{1-6}$ aliphatic, optionally substituted phenyl, optionally substituted —O(Ph), optionally substituted —CH$_2$(Ph), optionally substituted —(CH$_2$)$_{1-2}$(Ph); optionally substituted —CH═CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of R$^+$, on the same substituent or different substituents, taken together with the atom(s) to which each R$^+$ group is bound, form a 5-8-membered heterocyclyl, aryl, or heteroaryl ring or a 3-8-membered cycloalkyl ring having 0-3 heteroatoms independently selected from nitrogen, oxygen, or sulfur. Optional substituents on the aliphatic group or the phenyl ring of R$^+$ are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo(C$_{1-4}$ aliphatic), wherein each of the foregoing C$_{1-4}$aliphatic groups of R$^+$ is unsubstituted.

As detailed above, in some embodiments, two independent occurrences of R$^\circ$ (or R$^+$, or any other variable similarly defined herein), are taken together with the atom(s) to which each variable is bound to form a 5-8-membered heterocyclyl, aryl, or heteroaryl ring or a 3-8-membered cycloalkyl ring having 0-3 heteroatoms independently selected from nitrogen, oxygen, or sulfur. Exemplary rings that are formed when two independent occurrences of R$^\circ$ (or R$^+$, or any other variable similarly defined herein) are taken together with the atom(s) to which each variable is bound include, but are not limited to the following: a) two independent occurrences of R$^\circ$ (or R$^+$, or any other variable similarly defined herein) that are bound to the same atom and are taken together with that atom to form a ring, for example, N(R°)$_2$, where both occurrences of R° are taken together with the nitrogen atom to form a piperidin-1-yl, piperazin-1-yl, or morpholin-4-yl group; and b) two independent occurrences of R° (or R⁺, or any other variable similarly defined herein) that are bound to different atoms and are taken together with both of those atoms to form a ring, for example where a phenyl group is substituted with two occurrences of OR°

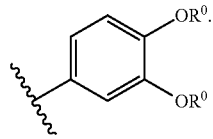

these two occurrences of R° are taken together with the oxygen atoms to which they are bound to form a fused 6-membered oxygen containing ring:

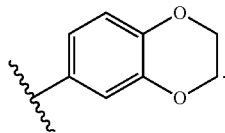 [SMILES: *c1ccc2c(c1)OCCO2]

It will be appreciated that a variety of other rings can be formed when two independent occurrences of R° (or R⁺, or any other variable similarly defined herein) are taken together with the atom(s) to which each variable is bound and that the examples detailed above are not intended to be limiting.

An alkyl or aliphatic chain can be optionally interrupted with another atom or group. This means that a methylene unit of the alkyl or aliphatic chain is optionally replaced with said other atom or group. Examples of such atoms or groups would include, but are not limited to, —NR—, —O—, —S—, —CO$_2$—, —OC(O)—, —C(O)CO—, —C(O)—, —C(O)NR—, —C(=N—CN), —NRCO—, —NRC(O)O—, —SO$_2$NR—, —NRSO$_2$—, —NRC(O)NR—, —OC(O)NR—, —NRSO$_2$NR—, —SO—, or —SO$_2$—, wherein R is defined herein. Unless otherwise specified, the optional replacements form a chemically stable compound. Optional interruptions can occur both within the chain and at either ends of the chain; both at the point of attachment and also at the terminal end. Two optional replacements can also be adjacent to each other within a chain. Unless otherwise specified, if the replacement or interruption occurs at the terminal end, the replacement atom is bound to an H on the terminal end. For example, if —CH$_2$CH$_2$CH$_3$ were optionally interrupted with —O—, the resulting compound could be —OCH$_2$CH$_3$, —CH$_2$OCH$_3$, or —CH$_2$CH$_2$OH.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

The present invention relates to a compound of formula I:

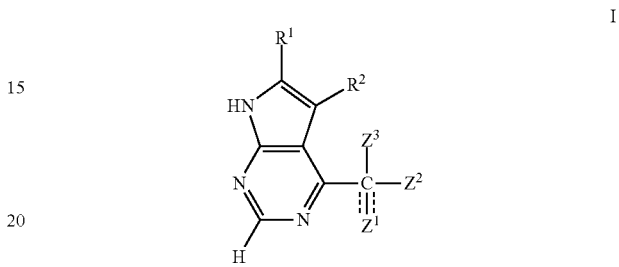

or a pharmaceutically acceptable salt thereof, wherein:
wherein
R$^1$ is H, —NO$_2$, —CN, —OCF$_3$, halogen, or amino; or C$_{1-6}$aliphatic, C$_{3-7}$cycloaliphatic, C$_{1-6}$alkoxy, or C$_{1-4}$haloalkyl optionally substituted with 0-10 J$^R$ groups;
R$^2$ is H, —NO$_2$, —CN, —OCF$_3$, halogen, or amino; or C$_{1-6}$aliphatic, C$_{3-7}$cycloaliphatic, C$_{1-6}$alkoxy, or C$_{1-4}$haloalkyl optionally substituted with 0-10 J$^R$ groups;
Z$^1$ is C$_{1-6}$aliphatic or C$_{3-10}$cycloaliphatic optionally substituted with 0-10 J$^Z$ groups; if the bond between Z$^1$ and C is a double bond, then Z$^1$ may also be =O, =NR, or =C(R)$_2$;
Z$^2$ is H or halogen; or C$_{1-10}$haloalkyl, C$_{1-4}$haloalkoxy, Y, —(V$_n$)—CN, —(V$_n$)—NO$_2$, —(V$_n$)—OH, —(V$_n$)—(C$_{1-6}$aliphatic), —(V$_n$)—(C$_{3-12}$heterocyclyl), —(V$_n$)—(C$_{6-10}$aryl), —(V$_n$)-(5-10 membered heteroaryl), or —(V$_n$)—(C$_{3-10}$cycloaliphatic) optionally substituted with 0-10 J$^Z$ groups; or
Z$^1$ and Z$^2$, together with the carbon atom to which they are attached, form ring Q;
Z$^3$ is H or C$_{1-6}$alkyl optionally substituted with 0-3 J$^Z$ groups; or
Z$^1$, Z$^2$, and Z$^3$, together with the carbon atom to which they are attached, form an 6-14 membered saturated, partially saturated, or unsaturated bicyclic ring having 0-3 heteroatoms; wherein
if the bond between Z$^1$ and C is a triple bond, then Z$^2$ is absent; and
if the bond between Z$^1$ and C is a double bond or a triple bond, then Z$^3$ is absent;
Q is a 3-8 membered saturated or partially saturated monocyclic ring having 0-3 heteroatoms selected from nitrogen, oxygen, or sulfur, wherein said Q is optionally and independently fused to Q$^1$ or Q$^2$; or to both Q$^1$ and Q$^2$; wherein said Q is optionally substituted with 0-4 J$^Q$ groups;
Q$^1$ is a 3-8 membered saturated, partially saturated, or unsaturated monocyclic ring having 0-3 heteroatoms selected from nitrogen, oxygen, or sulfur, wherein said Q$^1$ group is optionally substituted with 0-4 J$^Q$ groups;
Q$^2$ is a 3-8 membered saturated, partially saturated, or unsaturated monocyclic ring having 0-3 heteroatoms selected from nitrogen, oxygen, or sulfur wherein said Q$^2$ group is optionally substituted with 0-4 J$^Q$ groups;

R is H, optionally substituted $C_{1-6}$ aliphatic, $C_{3-10}$ cycloaliphatic, $C_{6-10}$ aryl, 5-14 membered heteroaryl, or 5-14 membered heterocyclyl; or two R groups, on the same substituent or different substituents, together with the atom(s) to which each R group is bound, form an optionally substituted 3-14 membered saturated, partially unsaturated, or fully unsaturated monocyclic, bicyclic, or tricyclic ring having 0-4 heteroatoms independently selected from nitrogen, oxygen, or sulfur wherein said R is optionally substituted with 0-10 $J^R$ groups;

each $J^Q$ and $J^Z$ substituent on an unsaturated carbon atom is independently selected from hydrogen, —$OCF_3$, $C_{1-6}$haloalkyl, $N(R)_2$, OR, halogen, Y, —$(V_n)$—CN, —$(V_n)$—$NO_2$, —$(V_n)$—OH, —$(V_n)$—$(C_{1-6}$aliphatic), —$(C_{3-10}$cycloaliphatic)—C(O)R, —$(C_{3-10}$-cycloaliphatic)-$(C_{3-12}$heterocyclyl); —$(V_n)$—$(C_{3-12}$heterocyclyl), —$(V_n)$—$(C_{6-10}$aryl), —$(V_n)$-(5-10 membered heteroaryl), —$(V_n)$—$(C_{3-10}$cycloaliphatic); wherein each $J^Q$ and $J^Z$ is optionally substituted with up to 10 $J^R$ groups; each $J^Q$ and $J^Z$ substituent on a saturated carbon atom is selected from those listed above for an unsaturated carbon and also the following: =O, =NN($R^a$)$_2$, =NNHC(O)$R^a$, =NNHCO$_2$($C_{1-4}$alkyl), =NNHSO$_2$($C_{1-4}$alkyl), and =$NR^a$ wherein each $J^Q$ and $J^Z$ is optionally substituted with up to 10 $J^R$ groups;

each $J^Q$ and $J^Z$ substituent on a nitrogen atom is independently selected from hydrogen, Y, —$(V_n)$—CN, —$(V_n)$—$NO_2$, —$(V_n)$—OH, —$(V_n)$—$(C_{1-6}$aliphatic), —$(C_{3-10}$cycloaliphatic)-C(O)R, —$(C_{3-10}$cycloaliphatic)-$(C_{3-12}$heterocyclyl), —$(V_n)$—$(C_{3-12}$heterocyclyl), —$(V_n)$—$(C_{6-10}$aryl), —$(V_n)$-(5-10 membered heteroaryl), —$(V_n)$—$(C_{3-10}$cycloaliphatic); wherein two $J^Z$ groups, on the same substituent or different substituents, together with the atom(s) to which each $J^Z$ group is bound, can optionally form an optionally substituted 3-14 membered saturated, partially unsaturated, or fully unsaturated monocyclic, bicyclic, or tricyclic ring having 0-4 heteroatoms independently selected from nitrogen, oxygen, or sulfur; wherein each $J^Q$ and $J^Z$ is optionally substituted with up to 10 $J^R$ groups;

$J^R$ is selected from halogen, —$N(R^b)_2$, $SR^b$, $OR^b$, oxo, $C_{1-4}$haloalkoxy, $C_{1-4}$haloalkyl, L, -$(L_n)$-$(C_{1-6}$alkyl), -$(L_n)$-$(C_{3-12}$heterocyclyl), -$(L_n)$-$(C_{6-10}$aryl), -$(L_n)$-(5-10 membered heteroaryl), -$(L_n)$-$(C_{3-10}$cycloalipahtic), -$(L_n)$-$NO_2$, -$(L_n)$-CN, -$(L_n)$-OH, —$CO_2R^b$, —$COR^b$, —$OC(O)R^b$, —$NC(O)R^b$;

L is $C_{1-10}$alkyl wherein up to three methylene units are replaced by —$NR^b$—, —O—, —S—, —$CO_2$—, —OC(O)—, —C(O)CO—, —C(O)—, —C(O)$NR^b$—, —C(=N—CN), —$NR^b$CO—, —$NR^b$C(O)O—, —$SO_2NR^b$—, —$NR^bSO_2$—, —$NR^bC(O)NR$—, —OC(O)$NR^b$—, —$NR^bSO_2NR^b$—, —SO—, or —$SO_2$—;

V is $C_{1-10}$aliphatic wherein up to three methylene units are replaced by $G^V$, wherein $G^V$ is selected from —NR—, —O—, —S—, —$CO_2$—, —OC(O)—, —C(O)CO—, —C(O)—, —C(O)NR—, —C(=N—CN), —NRCO—, —NRC(O)O—, —$SO_2NR$—, —$NRSO_2$—, —NRC(O)NR—, —OC(O)NR—, —$NRSO_2NR$—, —SO—, or —$SO_2$—;

Y is $C_{1-10}$aliphatic, wherein up to three methylene units are replaced by $G^Y$ wherein $G^Y$ is selected from —NR—, —O—, —S—, —$CO_2$—, —OC(O)—, —C(O)CO—, —C(O)—, —C(O)NR—, —C(=N—CN), —NRCO—, —NRC(O)O—, —$SO_2NR$—, —$NRSO_2$—, —NRC(O)NR—, —OC(O)NR—, —$NRSO_2NR$—, —SO—, or —$SO_2$—;

$R^a$ is hydrogen or $C_{1-6}$ aliphatic group optionally substituted with 0-3 $J^R$ groups;

$R^b$ is hydrogen or an unsubstituted $C_{1-6}$ aliphatic group;

n is 0 or 1;

provided that:

when $R^1$ and $R^2$ are H, and $Z^2$ and $Z^3$ are H, then $Z^1$ is not methyl;

when $R^1$ is $CH_3$ and $R^2$ is H, then $Z^1$, $Z^2$, and $Z^3$ are not all H;

when $R^1$ and $R^2$ are H, and $Z^2$ and $Z^3$ are H, then $Z^1$ is not unsubstituted phenyl, 4-pyridyl, or one of the structures shown below:

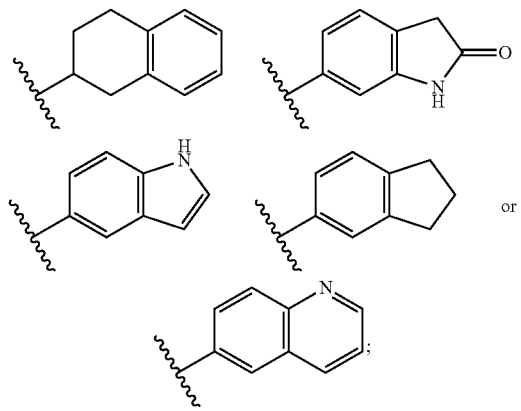

and when $R^1$ and $R^2$ are H, $Z^1$ and $Z^2$ taken together are not —C≡C—$CH_2CH_2$COOH.

According to one embodiment of this invention, $Z^1$, $Z^2$, and $Z^3$, together with the carbon atom to which they are attached, form the bicyclic ring shown in Formula I:

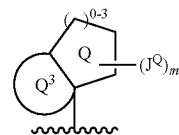

I wherein $Q^3$ is 3-8 membered saturated, unsaturated, or partially saturated monocyclic ring;

Q and $Q^3$ are each optionally and independently substituted with 0-4 $J^Q$ groups.

In one embodiment, $Q^3$ is a cyclopropyl group optionally substituted with 0-2 $J^Q$ groups as shown in formula II:

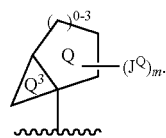

According to another embodiment of this invention, $Z^1$ and $Z^2$, together with the carbon atom to which they are attached, form a monocyclic, bicyclic, or tricyclic ring as shown in formula III:

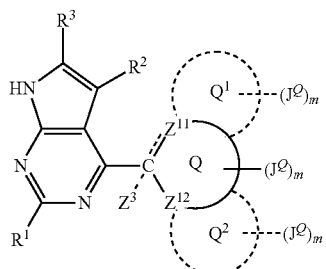

III wherein
$Z^{11}$ is selected from C, N, O, or S;
$Z^{12}$ is selected from C, N, O, or S;
Q is a 3-8 membered saturated or partially saturated monocyclic ring, optionally fused to $Q^1$ or $Q^2$;
$Q^1$ and $Q^2$ are each independently a 3-8 membered saturated, unsaturated, or partially saturated monocyclic ring;
Q, $Q^1$ and $Q^2$ each independently contain up to three heteroatoms selected from O, N, or S;
m is is 0-4; and is independently selected for Q, $Q^1$ and $Q^2$; and
$Z^3$ is H; or if the bond between C and $Z^{11}$ is a double bond, then $Z^3$ is absent.

In some embodiments, $Z^{11}$ and $Z^{12}$ are each independently carbon.

In one embodiment, Q is $C_{3-7}$ monocycle and $Q^1$ and $Q^2$ are absent.

In another embodiment, Q and $Q^1$ together form a fused 6-14 membered bicyclic ring and $Q^2$ is absent.

In yet another embodiment, Q, $Q^1$, and $Q^2$ together form a fused 8-20 membered tricyclic ring.

In one embodiment, of the invention $Z^{12}$ is carbon and the fused ring of Q, $Q^1$, and optionally $Q^2$ is as shown in Formula IV:

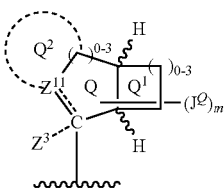

IV wherein Q, $Q^1$, and $Q^2$ each independently and optionally contain
a) 0-2 heteroatoms selected from O, N, or S; and
b) 0-4 $J^Q$ substituents.

In one embodiment, the hydrogen atoms at the point of fusion between ring Q and ring $Q^1$ is in the cis conformation as shown in Formula V:

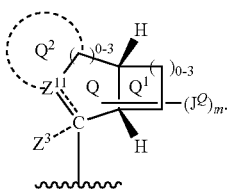

V

In another embodiment, the hydrogen atoms at the point of fusion between ring Q and ring $Q^1$ are in the trans conformation.

In one embodiment, C—$Z^{11}$ is a single bond.

In another embodiment, C=$Z^{11}$ is a double bond.

In certain embodiments, ring Q contains up to two heteroatoms. In other embodiments, ring Q contains one heteroatom; and in yet other embodiments, ring Q contains zero heteroatoms.

In one embodiment, Q contains two heteroatoms and each of said heteroatoms are independently selected from nitrogen, sulfur, or oxygen; preferably nitrogen and sulfur; more preferably, nitrogen. In some embodiments, both heteroatoms are nitrogen. In other embodiments, one is nitrogen and the other is sulfur. In some embodiments, one heteroatom is nitrogen and the other is oxygen. In yet other embodiments, one heteroatom is nitrogen and the other is sulfur.

In another embodiment, Q contains one heteroatom selected from O, N, or S. In some embodiments, the heteroatom is oxygen; in other embodiments, the heteroatom is nitrogen; in yet other embodiments, the heteroatom is sulfur. In some embodiments, the sulfur is optionally substituted with 0,1, or 2 oxo groups.

Examples of heterocyclic groups include piperidine, piperazine, morpholine, thiomorpholine, and pyrrolidine.

In some embodiments, ring Q is a 5-7 membered cycloaliphatic. Examples of cycloaliphatic groups include cyclohexane, cyclopentane, cyclohexene, and cyclopentene.

In other embodiments, $Q^1$ is a 6-membered aryl or 5-6 membered heteroaryl ring. Examples of aryl or heteroaryl rings include include phenyl, pyridine, pyrimidine, thiophene, thiazole, tetrazole, triazole, pyrrole, furan, and pyrazole.

In some embodiments, $Q^1$ is a 3-7 membered cycloaliphatic ring. Examples of cycloaliphatic rings include cyclohexane, cyclopentane, cyclohexene, cyclopentene, cycloheptene, cycloheptane, cyclopropane, cyclobutane, cyclopropene, and cyclobutene.

In other embodiment, $Q^1$ is a 3-7 membered heterocyclic ring. Examples of heterocyclic groups include piperidine, piperazine, morpholine, thiomorpholine, pyrrolidine, homopiperidine, and homopiperazine.

In one embodiment, Q or Q-$Q^1$ is represented by the following structures:

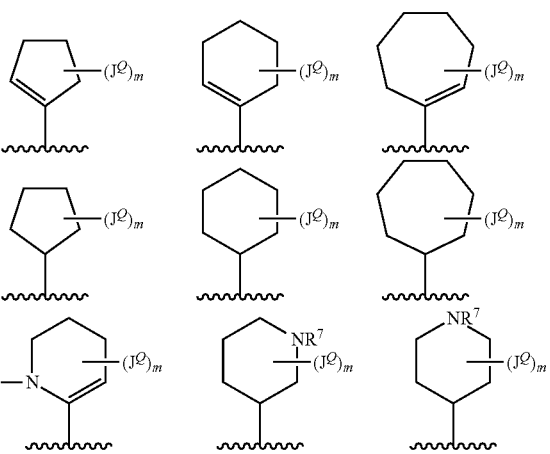

-continued wherein both $R^7$ and $J^Q$ are each independently selected from hydrogen, Y, —$(V_n)$—CN, —$(V_n)$—NO$_2$, —$(V_n)$—OH, —$(V_n)$—$(C_{1-6}$aliphatic), —$(V_n)$—$(C_{3-12}$heterocyclyl), —$(V_n)$—$(C_{6-10}$aryl), —$(V_n)$-(5-10 membered heteroaryl), —$(V_n)$—$(C_{3-10}$cycloaliphatic), and —$(C_{3-10}$cycloaliphatic)-$(C_{3-12}$heterocyclyl);
  wherein for each Q and Q$^1$, m is independently 0-3; and each $R^7$ and $J^Q$ is optionally and independently substituted with 0-10 $J^R$ groups.

In one embodiment m is 0, 1, or 2. In another embodiment, m is 1 or 2. In some embodiments, m is 0; in other embodiments, m is 1; in yet other embodiments, m is 2.

In some embodiments, $J^Q$ is Y, —$(V^1{}_n)$—CN, —$(V^1{}_n)$—NO$_2$, —$(V^1{}_n)$—OH, —$(V^1{}_n)$—$(C_{1-6}$aliphatic), —$V^1{}_n$—$(C_{3-12}$heterocyclyl), —$(V^1{}_n)$—$(C_{6-10}$aryl), —$(V^1{}_n)$-(5-10 membered heteroaryl), —$(V^1{}_n)$—$(C_{3-10}$cycloaliphatic), or —$(C_{3-10}$cycloaliphatic)-$(C_{3-12}$heterocyclyl); wherein
  $V^1$ is -$G^V$-$(X)_p$, wherein X is a $C_{1-9}$aliphatic wherein up to two methylene units are replaced by —NR—, —O—, —S—, —CO$_2$—, —OC(O)—, —C(O)CO—, —C(O)—, —C(O)NR—, —C(=N—CN), —NRCO—, —NRC(O)O—, —SO$_2$NR—, —NRSO$_2$—, —NRC(O)NR—, —OC(O)NR—, —NRSO$_2$NR—, —SO—, or —SO$_2$—;

p is 0 or 1;

n is 0 or 1;

$G^V$ is selected from C=O, C(=O)NR, S(O)$_2$ or S(O); and said $J^Q$ is optionally substituted with 0-10 $J^R$ groups.

In one embodiment, X is optionally substituted $C_{1-4}$aliphatic. In some embodiments, X is optionally substituted $C_{1-4}$alkyl. In some embodiments, X is optionally substituted $C_{1-2}$alkyl.

In some embodiments, n is 0. In other embodiments, n is 1. In certain embodiments, p is 0. In other embodiments, p is 1.

In some embodiments, $J^Q$ is optionally substituted with 0-10 $J^R$ groups. In some embodiments, 0-5 $J^R$ groups; in other embodiments, 0-3 $J^R$ groups; and in yet other embodiments, 0-2 $J^R$ groups; In some embodiments, one $J^R$ group, and in certain embodiments, 0 $J^R$ groups.

In one embodiment, $G^V$ is C=O.

In another embodiment of this invention, $R^1$ and $R^2$ are each independently H, halogen, $C_{1-4}$alkyl, or $C_{1-4}$alkoxy. In one embodiment, $R^1$ and $R^2$ are each independently H.

In some embodiments, $R^7$ is independently selected from Y, —$(V^1{}_n)$—CN, —$(V^1{}_n)$—NO$_2$, —$(V^1{}_n)$—OH, —$(V^1{}_n)$—$(C_{1-6}$aliphatic), —$(V^1{}_n)$—$(C_{3-12}$heterocyclyl), —$(V^1{}_n)$—$(C_{6-10}$aryl), —$(V^1{}_n)$-(5-10 membered heteroaryl), —$(V^1{}_n)$—$(C_{3-10}$cycloaliphatic), or —$(C_{3-10}$cycloaliphatic)-$(C_{3-12}$heterocyclyl); wherein
  $V^1$ is -$G^V$-$(X)_p$ wherein X is a $C_{1-9}$aliphatic wherein up to two methylene units are replaced by —NR—, —O—, —S—, —CO$_2$—, —OC(O)—, —C(O)CO—, —C(O)—, —C(O)NR—, —C(=N—CN), —NRCO—, —NRC(O)O—, —SO$_2$NR—, —NRSO$_2$—, —NRC(O)NR—, —OC(O)NR—, —NRSO$_2$NR—, —SO—, or —SO$_2$—;

p is 0 or 1;

n is 0 or 1; and $G^V$ is selected from C=O, C(=O)NR, S(O)$_2$ or S(O).

Representative examples of compounds of formula I are set forth in Table 1.

TABLE 1

Formula VI wherein A is selected from:

TABLE 1-continued
Formula VI
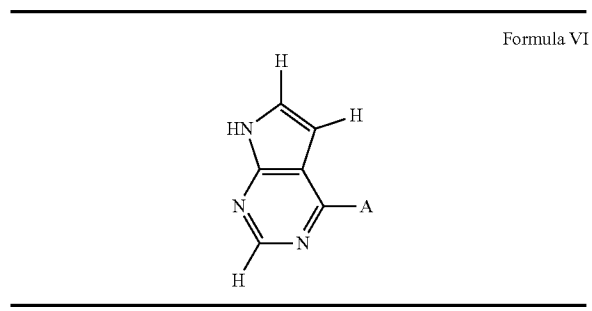
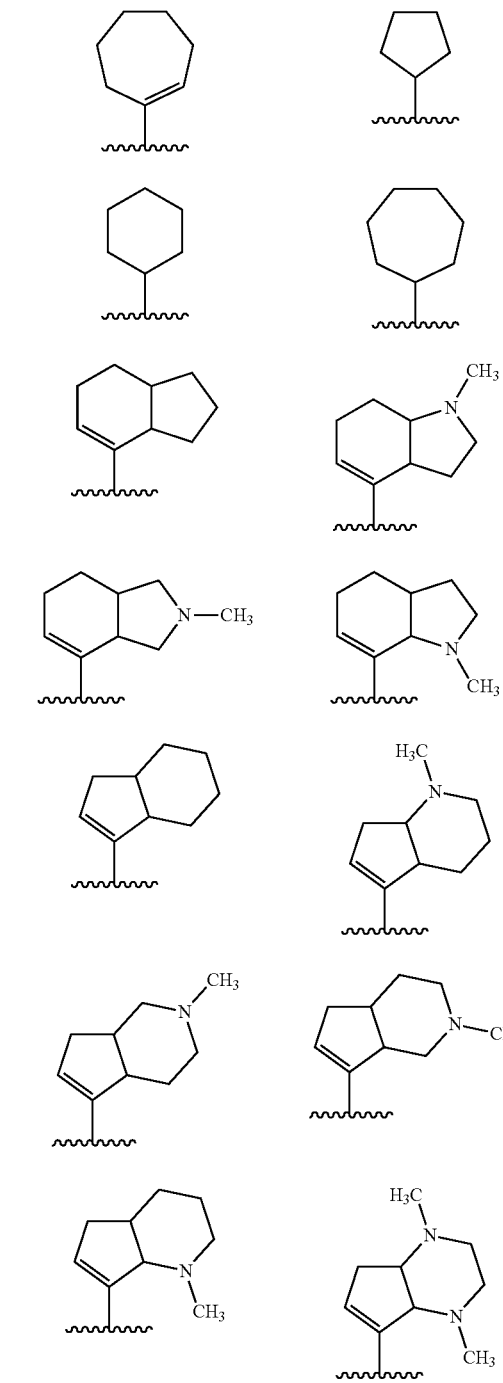
TABLE 1-continued
Formula VI
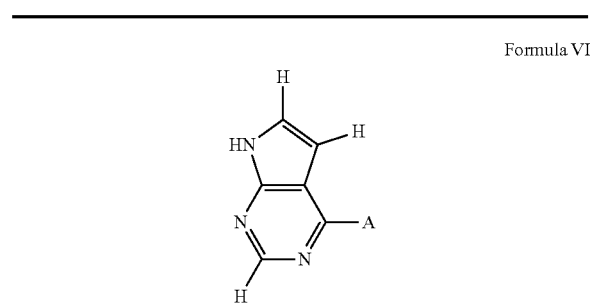
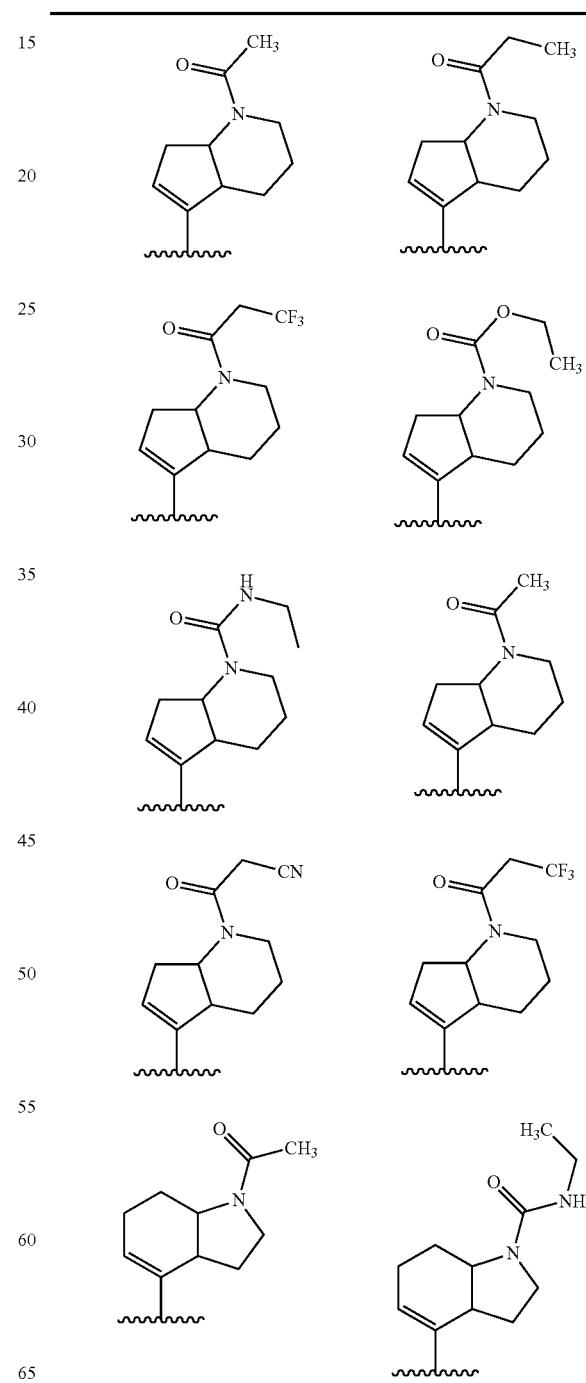

TABLE 1-continued

Formula VI

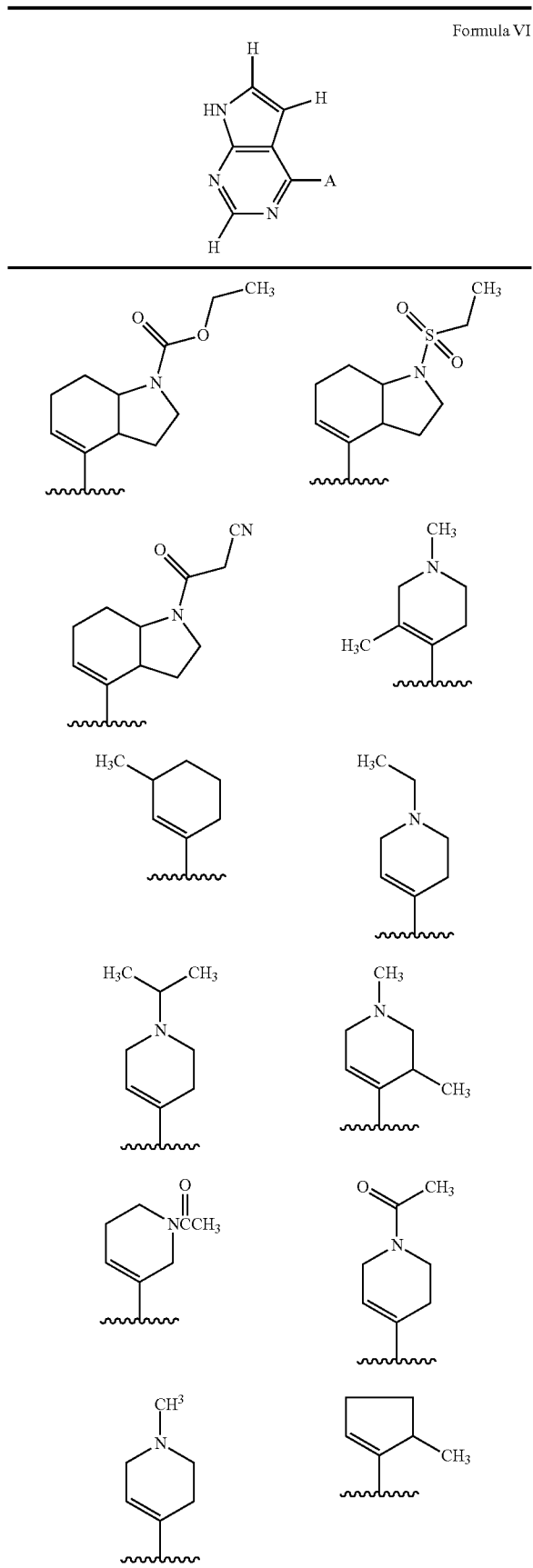

In another embodiment of this invention, $Z^1$ and $Z^2$ do not join to form a ring and $Z^3$ is H or is absent.

In one embodiment, $Z^1$ is H or $C_{1-6}$aliphatic optionally substituted with 0-3 $J^Z$ groups. In some embodiments, $Z^1$ is H.

In certain embodiments, C≡$Z^1$ is a triple bond, and $Z^2$ and $Z^3$ are absent.

In other embodiments, C=$Z^1$ is a double bond and $Z^3$ is absent.

In certain embodiments, $Z^1$ is O; in other embodiments, $Z^1$ is $CH_2$.

In certain embodiments, $Z^2$ optionally substituted Y, —$(V_n)$—$(C_{1-6}$aliphatic), —$(V_n)$—$(C_{3-12}$heterocyclyl), —$(V_n)$—$(C_{6-10}$aryl), —$(V_n)$-(5-10 membered heteroaryl), or —$(V_n)$—$(C_{3-10}$cycloaliphatic). In some embodiments, is 0; In other embodiments, n is 1.

In other embodiments, $Z^2$ is an optionally substituted 5-7 membered monocycle selected from heterocyclyl, cycloaliphatic, aryl, or heteroaryl; preferably a 5-7 membered fully or partially saturated monocycle selected from heterocyclyl or cycloaliphatic; more preferably, a 6-membered monocycle with 0-2 nitrogen atoms. In one preferred embodiment of this invention, $Z^2$ is piperidine optionally substituted with 0-3 $J^Z$ groups.

In some embodiments, $Z^2$ is optionally substituted —$(V_n)$—$(C_{3-10}$cycloaliphatic) wherein n is 0. In one embodiment, $Z^2$ is a bicyclo-octane ring. In another embodiment, $Z^2$ is a $C_{5-7}$cycloaliphatic. In yet another embodiment, $Z^2$ is a $C_{5-7}$cycloalkyl.

In one embodiment, $J^Z$ is halogen, $CF_3$, optionally substituted $C_{1-4}$haloalkyl, —$(V^1_n)$—CN, —$(V^1_n)$—$NO_2$, —$(V^1_n)$—OH, Y, —$(V^1_n)$—$(C_{3-12}$heterocyclyl), —$(V^1_n)$—$(C_{6-10}$aryl), —$(V^1_n)$-(5-10 membered heteroaryl), —$(V^1_n)$—$(C_{3-10}$cycloaliphatic), or —$(C_{3-10}$cycloaliphatic)-$(C_{3-12}$heterocyclyl); wherein $V^1$ is -$G^V$-$(X)_p$ wherein X is a $C_{1-9}$aliphatic wherein up to two methylene units are replaced by —NR—, —O—, —S—, —$CO_2$—, —OC(O)—, —C(O)CO—, —C(O)—, —C(O)NR—, —C(=N—CN), —NRCO—, —NRC(O)O—, —$SO_2$NR—, —$NRSO_2$—, —NRC(O)NR—, —OC(O)NR—, —$NRSO_2$NR—, —SO—, or —$SO_2$;

p is 0 or 1; and $G^V$ is selected from C═O, C(═O)NR, S(O)$_2$ or S(O).

In some embodiments, X is C$_{1-5}$aliphatic. In certain preferred embodiments, X is C$_{1-5}$alkyl. In other preferred embodiments, X is C$_{1-2}$alkyl.

In some embodiments, G$^v$ is selected from C═O, C(═O)NR, S(O)$_2$ or S(O). In certain embodiments, G$^v$ is C═O. In other embodiments, G$^v$ is C(═O)NR. In yet other embodiments, G$^v$ is S(O)$_2$ or S(O).

In some embodiments, J$^Z$ is halogen, CF$_3$, CN, optionally substituted C$_{1-6}$aliphatic, C$_{1-4}$haloalkyl, —(C$_{1-6}$alkyl)$_n$-R$^J$, —(C$_{1-6}$alkyl)$_n$-C(═O)R$^J$, —(C$_{1-6}$alkyl)$_n$-CON(R$^b$)R$^J$, —(C$_{1-6}$alkyl)$_n$-N(R$^b$)R$^J$, —(C$_{1-6}$alkyl)$_n$-OR$^J$, —(C$_{1-6}$alkyl)$_n$-OCON(R$^b$)R$^J$, —(C$_{1-6}$aliphatic)$_n$-S(O)N(R$^b$)R$^J$, —(C$_{1-6}$aliphatic)$_n$-S(O)R$^J$, or —(C$_{1-6}$aliphatic)$_n$-NHC(O)R$^J$;

wherein
R$^J$ is C$_{1-6}$aliphatic, C$_{3-12}$heterocyclyl, C$_{6-10}$aryl, 5-10 membered heteroaryl, or C$_{3-10}$cycloaliphatic; and
n is 0 or 1.

In other embodiments, J$^Z$ is halogen, OR$^J$, N(R$^b$)$_2$, CF$_3$, CN, optionally substituted C$_{1-6}$alkyl, —(C$_{1-6}$alkyl)$_n$-R$^J$, —C(═O)(C$_{1-6}$alkyl), —CON(R$^b$)(C$_{1-6}$alkyl), —OCON(R$^b$)(C$_{1-6}$alkyl), —S(O)N(R$^b$)(C$_{1-6}$alkyl), —S(O)(C$_{1-6}$alkyl), —NHC(O)C$_{1-6}$alkyl, —(C$_{1-6}$alkyl)-CONH, —(C$_{1-6}$alkyl)-N(R$^b$)$_2$, —(C$_{1-6}$alkyl)-OCON(R$^b$)R$^J$, —(C$_{1-6}$aliphatic)-S(O)N(R$^b$)(C$_{6-10}$aryl), —N(R$^b$)C(O)N(R$^b$)R$^J$, or —N(R$^b$)C(O)R$^b$.

In other embodiments, J$^Z$ is halogen, OR, N(R$^b$)$_2$, CF$_3$, CN, optionally substituted C$_{1-6}$alkyl, —(C$_{1-6}$alkyl)$_n$-R$^J$, C(═O)(C$_{1-6}$alkyl), CONH, —(C$_{1-6}$alkyl)-CONH, —(C$_{1-6}$alkyl)-N(R$^b$)$_2$, —(C$_{1-6}$alkyl)-OCON(R$^b$)R$^J$, —(C$_{1-6}$aliphatic)-S(O)N(R$^b$)(C$_{6-10}$aryl), —N(R$^b$)C(O)N(R$^b$)$_2$, or —(R$^b$)C(O)R$^b$.

In certain embodiments, R$^J$ is C$_{6-10}$aryl or 5-10 membered heteroaryl. In other embodiments, R$^J$ is C$_{1-6}$aliphatic or C$_{3-10}$cycloaliphatic. In some embodiments, R$^J$ is C$_{1-6}$aliphatic. In other embodiments, R$^J$ is C$_{3-10}$cycloaliphatic.

In some embodiments, n is 1. In other embodiments, n is 0.

In certain embodiments, J$^Z$ is optionally substituted —C(═O)(C$_{1-6}$alkyl), —C(═O)CH$_2$CN, or C$_{1-6}$alkyl.

Representative examples of compounds of formula I are set forth in Table 2.

TABLE 2

Formula VII

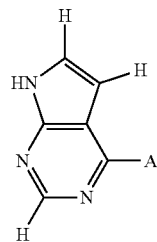

wherein A is selected from:

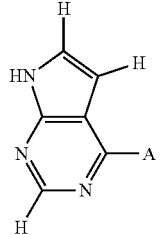

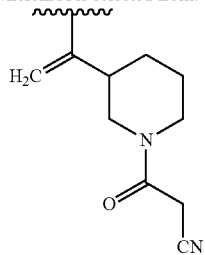 [SMILES: *C(=C)C1CCCN(C(=O)CC#N)C1]

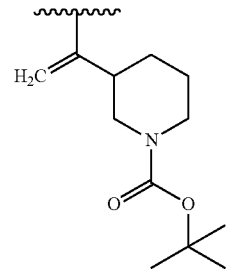

TABLE 2-continued

Formula VII

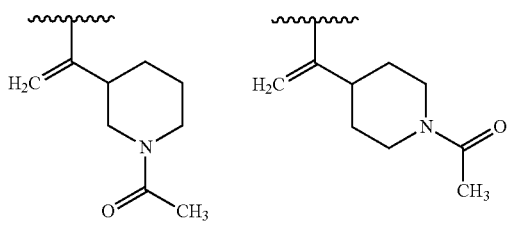

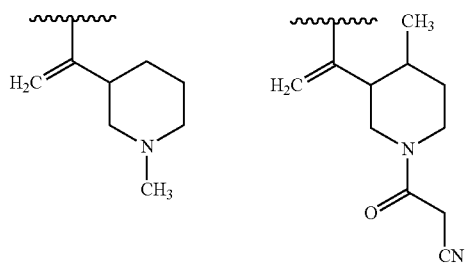

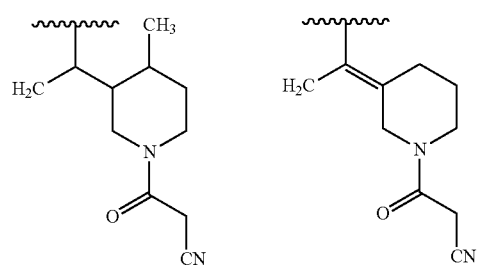

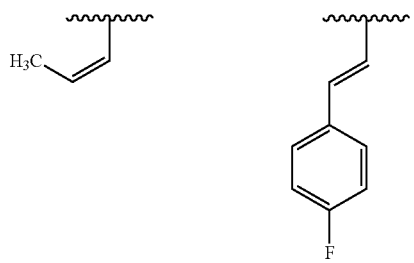

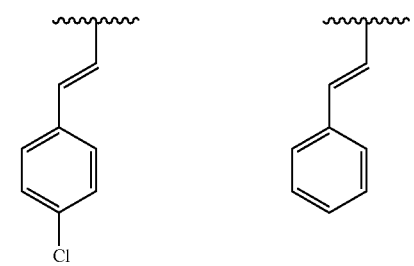

TABLE 2-continued
Formula VII
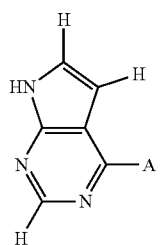
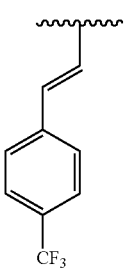 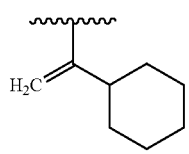 [SMILES: *C(=C)C1CCCCC1]
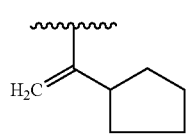 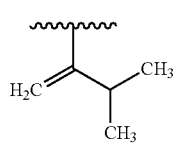
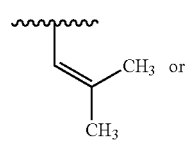 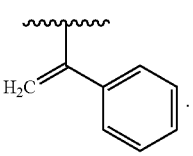
Representative examples of compounds of Formula I are set forth below in Table 3:
1
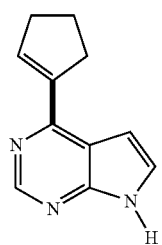
2
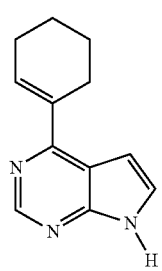
3
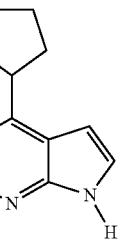
4
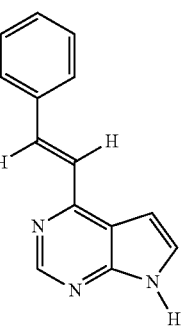
5
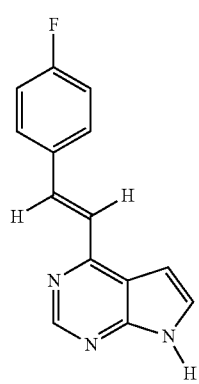
6
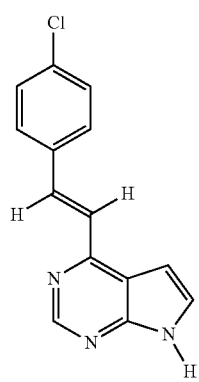

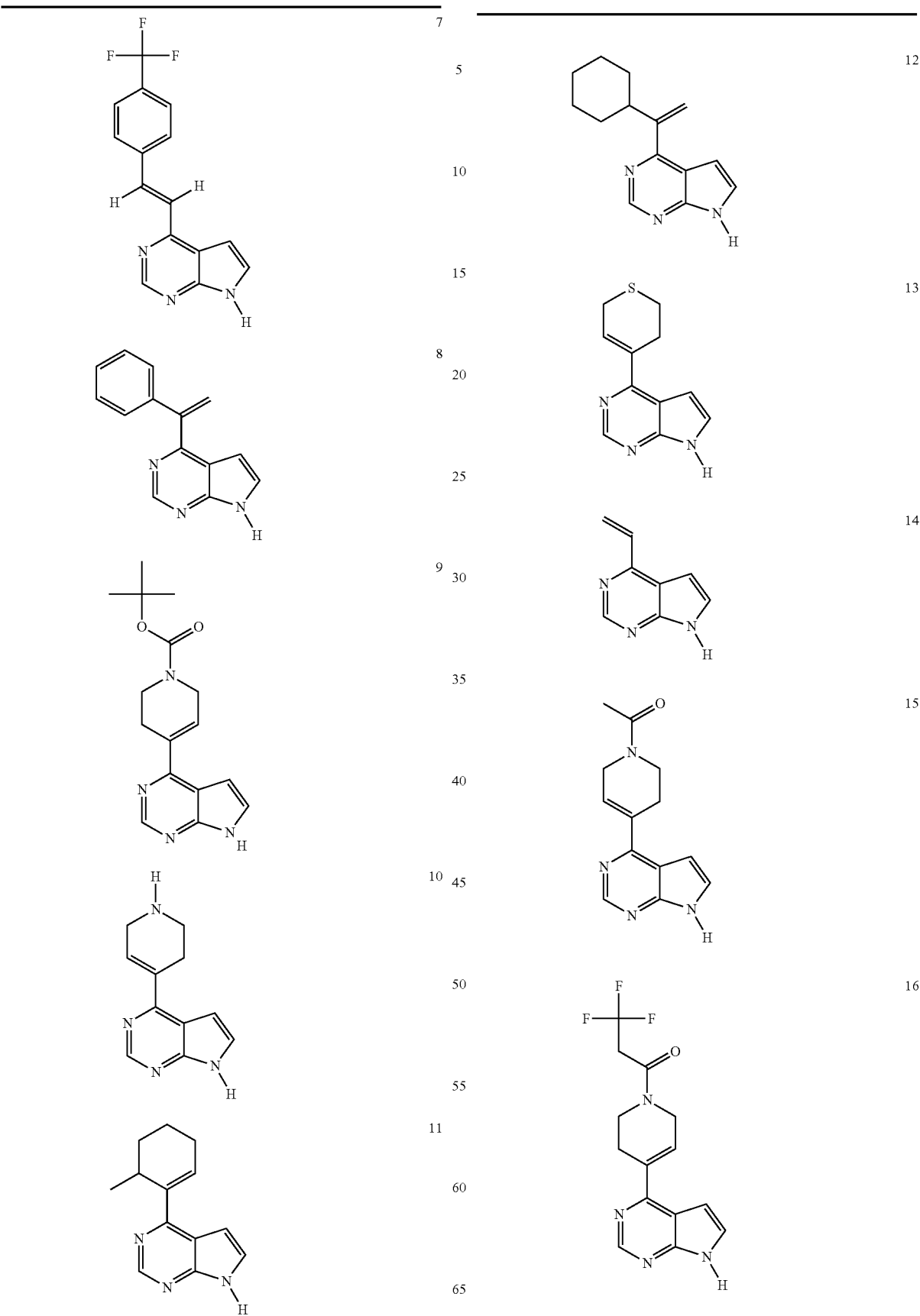

| 25 -continued | 26 -continued |
|---|---|
| 17 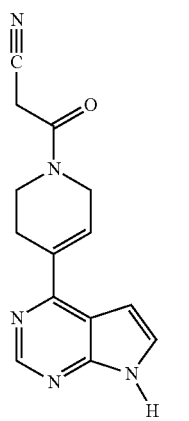 [SMILES: N#CCC(=O)N1CC=C(c2ncnc3[nH]ccc23)CC1] | 22 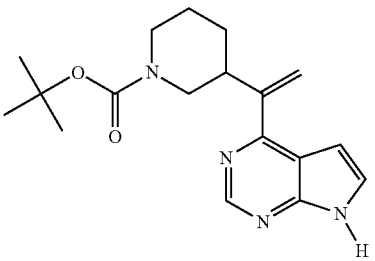 |
| 18 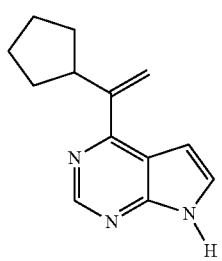 [SMILES: C=C(c1ncnc2[nH]ccc12)C1CCCC1] | 23 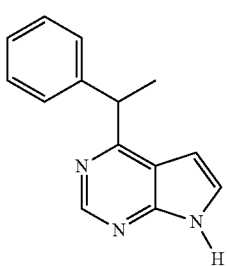 |
| 19 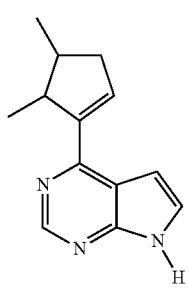 [SMILES: CC1CC=C(c2ncnc3[nH]ccc23)C1C] | 24 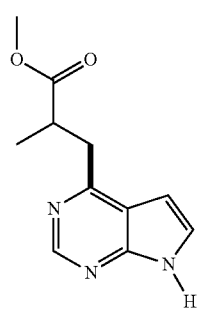 |
| 20 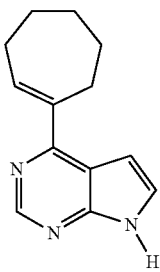 [SMILES: C1=C(c2ncnc3[nH]ccc23)CCCCC1] | 25 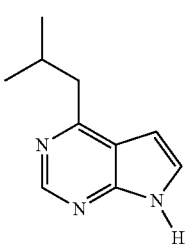 |
| 21 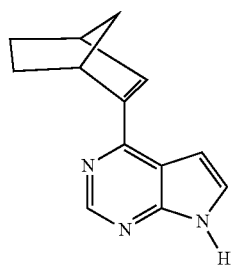 [SMILES: C1=C(c2ncnc3[nH]ccc23)C2CCC1C2] | 26 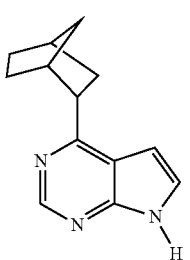 [SMILES: c1nc(C2CC3CCC2C3)c2cc[nH]c2n1] |

27
-continued

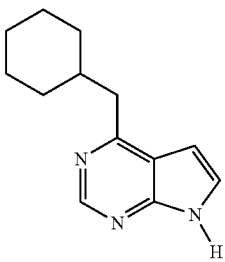 [SMILES: c1nc(CC2CCCCC2)c2cc[nH]c2n1]

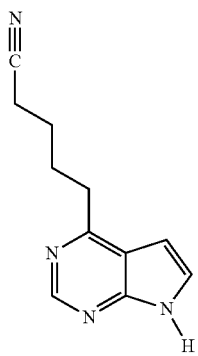 [SMILES: N#CCCCCc1ncnc2[nH]ccc12]

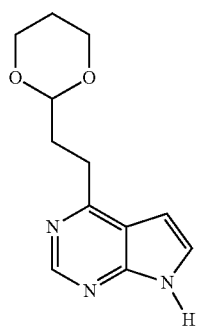 [SMILES: c1nc(CCC2OCCCO2)c2cc[nH]c2n1]

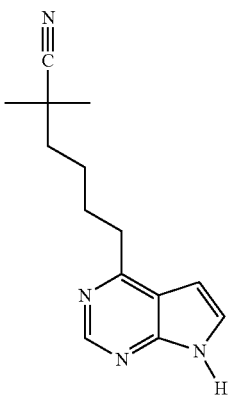 [SMILES: CC(C)(C#N)CCCCc1ncnc2[nH]ccc12]

28
-continued

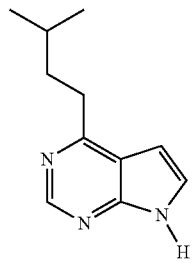

General Synthetic Methodology:

The compounds of this invention may be prepared in general by methods known to those skilled in the art for analogous compounds or by those methods depicted in the Examples below. In general, Example 1 depicts several methods for preparation of functionalized quinoxalines.

Although certain exemplary embodiments are depicted and described herein, it will be appreciated that a compounds of the invention can be prepared according to the methods described generally above using appropriate starting materials by methods genrally available to one of ordinary skill in the art.

All references provided in the synthetic schemes and examples are herein incorporated by reference. As used herein, all abbreviations, symbols and conventions are consistent with those used in the contemporary scientific literature. See, e.g., Janet S. Dodd, ed., *The ACS Style Guide: A Manual for Authors and Editors,* 2nd Ed., Washington, D.C.: American Chemical Society, 1997, herein incorporated in its entirety by reference. In addition, the following definitions describe terms and abbreviations used herein:

| | |
|---|---|
| Ts-Cl | p-toluenesulfonyl chloride (tosyl chloride) |
| DMF | dimethylformamide |
| Tf | triflate |
| LiHMDS | lithium hexamethyldisilazide |
| dppf | 1,1'-bis(diphenylphosphino)-ferrocene |
| Ac | acetyl |
| DME | 1,2-Dimethoxyethane |
| atm | atmospheres |
| EDCI | 1-Ethyl-3-(3-dimethylaminopropyl)carbodiimide Hydrochloride |
| DIEA | diisopropylethylamine |
| LiHMDS | Lithium Hexamethyldisilazane |
| THF | tetrahydrofuran |
| HEPES | 4-(2-hydroxyethyl)-1-piperazineethanesulfonic acid |
| Glu | glutamate |
| Tyr | tyrosine |
| ATP | adenosine triphosphate |
| Ph | phenyl |
| Me | methyl |
| BSA | bovine serum albumin |
| DTT | dithiothreitol |

Scheme 1

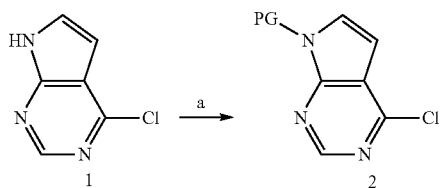

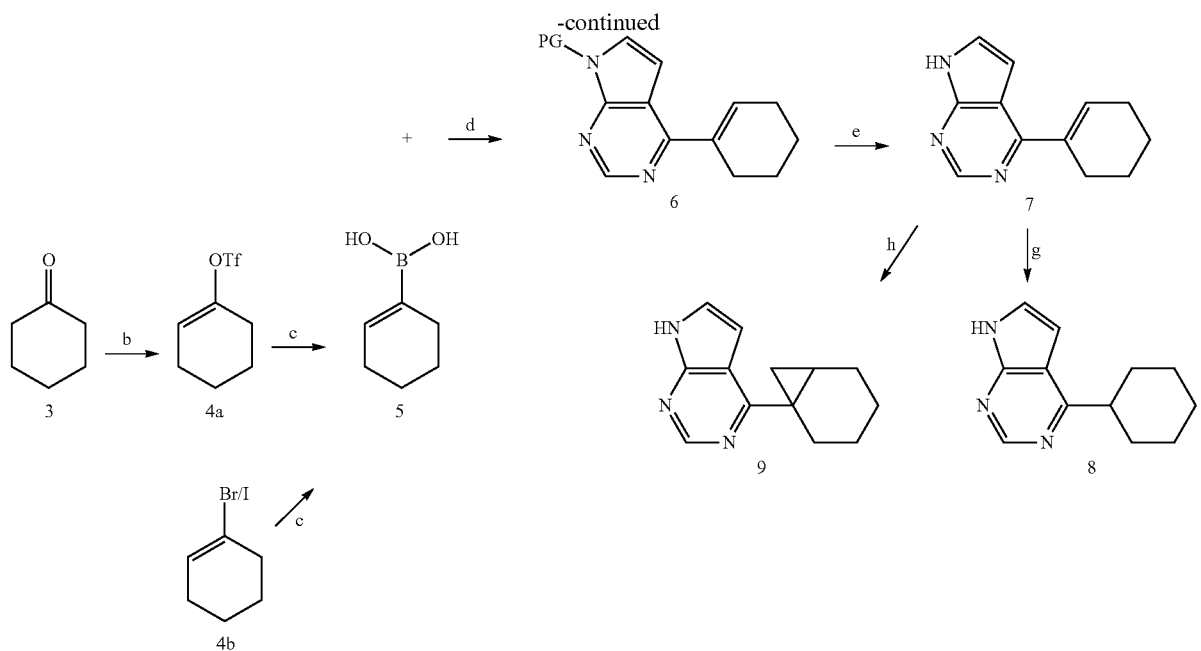

Scheme 1 is a representative scheme for the preparation of compounds of this invention. Compound 1, which is commercially available, can be protected by a suitable protecting group (e.g. Tosyl) as described in T. W. Greene & P. G. M Wutz, "Protective Groups in Organic Synthesis", 3$^{rd}$ Edition, John Wiley & Sons, Inc. (1999)) to form compound 2. Boronic acids/esters (5) can be prepared from the corresponding vinyl halides (4b) or vinyl triflates (4a) as described in Comins, D. L.; Dehghani, A. *Tetrahedron Lett.* 1992, 33, 6299-6302; McMurry, J. E.; Scott, W. J. *Tetrahedron Lett.*, 1983, 24, 979; Stang, P. J.; Fisk, P. J. *Synthesis*, 1980, 283; Stang, P. J.; Fisk, P. J. *Synthesis*, 1979, 438; Takagi, J.; Takahashi, K.; Ishiyama, T.; Miyaura, N. *J. Am. Chem. Soc.*, 2002, 124, 8001 and references therein. The Pd-mediated cross coupling of the N-protected halide (e.g. chloride) (2) and the boronic acid (3) in the presence of an appropriate base such as KOAc or $Na_2CO_3$ provides compounds of type (6) as described in A. Suzuki, H. C. Brown "Organic Synthesis Via Boranes; Volume 3: Suzuki Coupling" Aldrich Chemical Company: Milwaukee, Wis., 2003 and references therein. Deprotection under basic conditions (e.g. LiOH $_{(aq)}$ or NaOMe) then delivers (7). Hydrogenation with Pd-C under H2 atmosphere gives (8). Cyclopropanation of (7), as described in Reiser, Oliver "Cyclopropanation and other reactions of palladium-carbene (and carbyne) complexes" Handbook of Organopalladium Chemistry for Organic Synthesis (2002), 1 1561-1577, gives (9).

Scheme 2

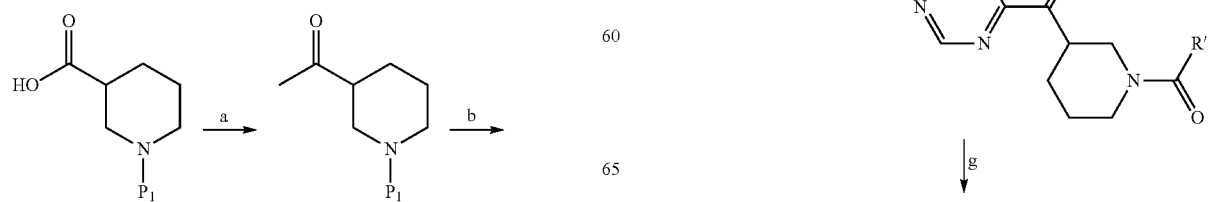

-continued

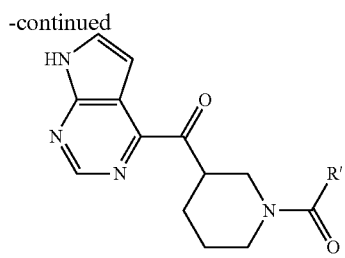

Conditions: (a) i: HCl-HNMeOMe, EDCI, DIEA; ii: MeMgBr;
(b) LiHMDS, PhNTf2,THF, -78° C.;
(c) bispinacolatoborane, Pd(dppf)$_2$Cl$_2$, KOAc then water;
(d) Pd(PPh$_3$)$_4$, KOAc, dioxane or DME, 100-180° C.;
(e) i: LiOH or NaOMe, ii: HCl,;
(f) R'COCl, R'OCOCl, or R'NCO; DIEA or R'OOH; EDCI; and DIEA /
wherein R'COCl, R'OCOCl, and R'NCO refer to suitable acid chlorides, oxalyl chlorides, and isocyanates which are either commercially available or can be made from commercially available starting materials.

Scheme 2 shows additional methods for the preparation of compounds of this invention. In addition to acid chlorides, isocyanates, and oxalyl chlorides, other compounds that react with amines can be used to form P$_1$ substitutions. Examples include, but are not limited to, R'-halogen, R'-tosyl, R'-mesylate, R'S(O)$_2$Cl, R'NS(O)$_2$Cl, R'OH, R'COOH, and R'CH$_2$-halogen. —C═CH$_2$ compounds can optionally be converted into —C═O compounds with ozonolysis (g).

Scheme 3

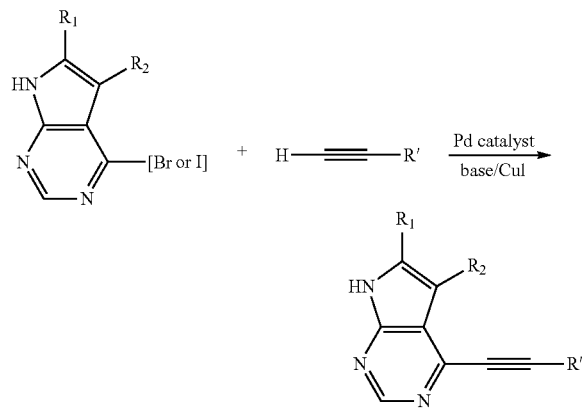

Scheme III shows an additional method for preparing compounds of this invention. The aryl bromide or iodide can be coupled with substituted terminal alkynes in the presence of palladium, base, and CuI under Sonogashira coupling conditions (Sonogashira, Kenkichi. "Palladium-catalyzed alkynylation" Editor(s): Negishi, Ei-ichi. Handbook of Organopalladium Chemistry for Organic Synthesis (2002), 1: 493-529. Publisher: John Wiley & Sons, Inc., Hoboken, N.J.) to form the product as shown. H═R' refers to suitable terminal alkynes which are either commercially available or can be made from commercially available starting materials.

Although certain exemplary embodiments are depicted and described above and herein, it will be appreciated that a compounds of the invention can be prepared according to the methods described generally above using appropriate starting materials by methods generally available to one of ordinary skill in the art.

Uses, Formulations and Administration

As discussed above, the present invention provides compounds that are inhibitors of protein kinases, including JAK family, ROCK and PKA kinases, particularly JAK2 and JAK3 kinases, and thus the present compounds are useful for the treatment of diseases, disorders, and conditions including, but not limited to, immunodeficiency disorders, inflammatory diseases, allergic diseases, autoimmune diseases, proliferative disorders, immunologically-mediated diseases, respiratory disorders. Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt of a compound of this invention.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$alkyl)$_4$ salts. This invention also envisions the quaternization of any basic nitrogen-containing groups of the compounds disclosed herein. Water or oil-soluble or dispersible products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, a method for the treatment or lessening the severity of a proliferative disorder, a cardiac disorder, a neurodegenerative disorder, an autoimmune disorder, a condition associated with organ transplant, an inflammatory disorder, or an immunologically mediated disorder is provided comprising administering an effective amount of a compound, or a pharmaceutically acceptable composition comprising a compound to a subject in need thereof. In certain embodiments of the present invention an "effective amount" of the compound or pharmaceutically acceptable composition is that amount effective for treating or lessening the severity of a proliferative disorder, a cardiac disorder, a neurodegenerative disorder, an autoimmune disorder, a condition associated with organ transplant, an inflammatory disorder, a psychotic disorder, a viral disease, a bone disorder or an immunologically mediated disorder. The compounds and compositions, according to the method of the present invention, may be administered using any amount and any route of administration effective for treating or lessening the severity of a proliferative disorder, a cardiac disorder, a neurodegenerative disorder, an autoimmune disorder, a condition associated with organ transplant, an inflammatory disorder, a psychotic disorder, a viral disease, a bone disorder or an immunologically mediated disorder. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium.

For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of protein kinases, particularly for the JAK family kinases, ROCK and PKA. In a specific embodiment, the compounds and compositions of the invention are inhibitors of JAK2 and JAK3. The compounds and compositions are useful for treating or lessening the severity of a disease, condition, or disorder where activation of a JAK family kinase, ROCK and/or PKA is implicated in the disease, condition, or disorder. In a particular embodiment, the compounds and compositions are useful for treating or lessening the severity of a disease, condition, or disorder where activation of JAK2 or JAK3 is implicated in the disease, condition, or disorder. When activation of JAK2, JAK3, ROCK or PKA is implicated in a particular disease, condition, or disorder, the disease, condition, or disorder may also be referred to as "JAK2-mediated disease", "JAK3-mediated disease", "ROCK-mediated disease" or "PKA-mediated disease", respectively. Accordingly, in another aspect, the present invention provides a method for treating or lessening the severity of a disease, condition, or disorder where activation of a JAK family kinase, ROCK or PKA, particularly JAK2 or JAK3, is implicated in the disease state.

The activity of a compound utilized in this invention as an inhibitor of a JAK family kinase, ROCK or PKA, particularly JAK2 or JAK3, may be assayed in vitro, in vivo or in a cell line. In vitro assays include assays that determine inhibition of either the phosphorylation activity or ATPase activity of activated JAK2, JAK3, ROCK or PKA. Alternate in vitro assays quantitate the ability of the inhibitor to bind to JAK2, JAK3, ROCK or PKA. Inhibitor binding may be measured by radiolabelling the inhibitor prior to binding, isolating the inhibitor/kinase complex and determining the amount of radiolabel bound. Alternatively, inhibitor binding may be determined by running a competition experiment where new inhibitors are incubated with the kinase of interest bound to known radioligands.

The term "detectably inhibit", as used herein means a detectable change in JAK2, JAK3, ROCK or PKA activity between a sample comprising said composition and JAK2, JAK3, ROCK or PKA and an equivalent sample comprising JAK2, JAK3, ROCK or PKA, respectively, in the absence of said composition.

The term "JAK3-mediated disease" or "JAK3-mediated condition", as used herein means any disease or other deleterious condition in which JAK3 is known to play a role. A JAK3-mediated condition or disease also means those diseases or conditions that are alleviated by treatment with a JAK3 inhibitor. Such conditions include, without limitation, immune responses such as allergic or type I hypersensitivity reactions, asthma, autoimmune diseases such as transplant rejection, graft versus host disease, rheumatoid arthritis, amyotrophic lateral sclerosis, and multiple sclerosis, neurodegenerative disorders such as Familial amyotrophic lateral sclerosis (FALS), as well as in solid and hematologic malignancies such as leukemias and lymphomas.

The term "JAK2-mediated disease" or "JAK2-mediated condition", as used herein means any disease or other deleterious condition in which JAK2 is known to play a role. A JAK2-mediated condition or disease also means those diseases or conditions that are alleviated by treatment with a JAK2 inhibitor. Such conditions include, without limitation, myeloproliferative disorders, including polycythemia vera, essential thrombocythemia, chronic idiopathic myelofibrosis, myeloid metaplasia with myelofibrosis, chronic myeloid leukemia, chronic myelomonocytic leukemia, chronic eosinophilic leukemia, hypereosinophilic syndrome and systematic mast cell disease.

The term "ROCK-mediated disease" or "ROCK-mediated condition", as used herein, means any disease or other deleterious condition in which ROCK is known to play a role. A ROCK-mediated condition or disease also means those diseases or conditions that are alleviated by treatment with a ROCK inhibitor. Such conditions include, without limitation, hypertension, angina, angina pectoris, cerebrovascular contraction, asthma, peripheral circulation disorder, premature birth, cancer, erectile dysfunction, arteriosclerosis, spasm (cerebral vasospasm and coronary vasospasm), retinopathy (e.g., glaucoma), inflammatory disorders, autoimmune disorders, AIDS, osteoporosis, myocardial hypertrophy, ischemia/reperfusion-induced injury, endothelial dysfunction, Alzheimer's disease, or benign prostatic hyperplasia. In other embodiments, such conditions in which ROCK is known to play a role include, without limitation, hypertension, cerebral vasospasm, coronary vasospasm, bronchial asthma, preterm labor, erectile dysfunction, glaucoma, vascular smooth muscle cell proliferation, myocardial hypertrophy, malignoma, ischemia/reperfusion-induced injury, endothelial dysfunction, Crohn's Disease and colitis, neurite outgrowth, Raynaud's Disease, angina, Alzheimer's disease, benign prostatic hyperplasia, or atherosclerosis.

The term "PKA-mediated disease" or "PKA-mediated condition", as used herein, means any disease or other deleterious condition in which PKA is known to play a role. The term PKA-mediated condition or disease also means those diseases or conditions that are alleviated by treatment with a PKA inhibitor. PKA-mediated diseases or conditions include, but are not limited to, proliferative disorders and cancer.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

Another aspect of the invention relates to inhibiting JAK2, JAK3, ROCK or PKA activity in a biological sample, which method comprises contacting said biological sample with a compound of formula I or a composition comprising said compound. The term "biological sample", as used herein, is an ex vivo or in vitro sample, and includes, without limitation, cell cultures or extracts thereof; biopsied material obtained from a mammal or extracts thereof; and blood, saliva, urine, feces, semen, tears, or other body fluids or extracts thereof.

Inhibition of JAK2, JAK3, ROCK or PKA kinase activity in a biological sample is useful for a variety of purposes that are known to one of skill in the art. Examples of such purposes include, but are not limited to, blood transfusion, organ-transplantation, biological specimen storage, and biological assays.

EXAMPLES

For Examples 1-7, 1H-NMR spectra were recorded at 500 MHz using a Bruker AMX 500 instrument. Mass spectrometry samples were analyzed on a MicroMass ZQ or Quattro II mass spectrometer operated in single MS mode with electrospray ionization. Samples were introduced into the mass spectrometer using flow injection (FIA) or chromatography. Mobile phase for all mass spectrometric analyses consisted of acetonitrile-water mixtures with 0.2% formic acid as a modifier. As used herein, the term "$R_{rt}$" refers to the HPLC retention time, in minutes, associated with the compound.

Example 1

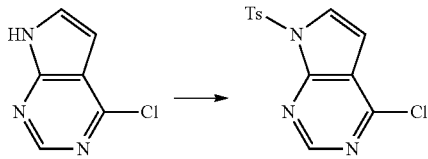 [SMILES: Clc1ncnc2[nH]ccc12 ; Cc1ccc(S(=O)(=O)n2ccc3c(Cl)ncnc32)cc1]

4-chloro-7-tosyl-7H-pyrrolo[2,3-d]pyrimidine

A slurry of 1 (307 mg, 2.00 mmol), Tosyl-chloride (418 mg, 2.20 mmol) and freshly ground $K_2CO_3$ (1.1 g, 8.0 mmol) in DMF (5.0 mL) was stirred at R.T. for 2 h. The mixture was partitioned between water and EtOAc and the organic phase was washed with brine (2×), dried ($Na_2SO_4$), filtered, and concentrated to provide the title compound (583 mg, 1.89 mmol, 95% yield) as a white solid.

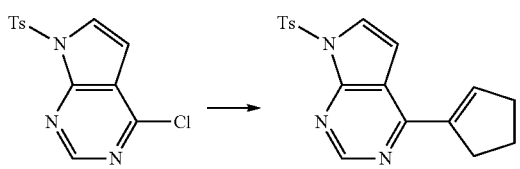 [SMILES: Cc1ccc(S(=O)(=O)n2ccc3c(Cl)ncnc32)cc1 ; Cc1ccc(S(=O)(=O)n2ccc3c(C4=CCCC4)ncnc32)cc1]

4-cyclopentenyl-7-tosyl-7H-pyrrolo[2,3-d]pyrimidine

A mixture of 4-chloro-7-tosyl-7H-pyrrolo[2,3-d]pyrimidine (62 mg, 0.20 mmol), cyclopenteneboronic acid (27 mg, 0.24 mmol), KOAc (78 mg, 0.80 mmol), and Pd(PPh3)4 (11 mg, 0.010 mmol), in dioxane (0.6 mL) was heated to 150° C. (MW, 600s) in a sealed tube. The reaction mixture was subjected to flash chromatography ($SiO_2$, 0-50% EtOAc-hexanes, gradient elution) to provide the title compound (55 mg, 0.16 mmol, 81 % yield) as a white solid.

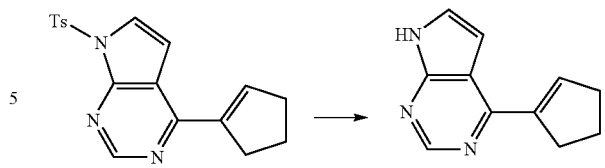

4-cyclopentenyl-7H-pyrrolo[2,3-d]pyrimidine (Compound 1)

A mixture of 4-cyclopentenyl-7-tosyl-7H-pyrrolo[2,3-d]pyrimidine (55 mg, 0.16 mmol) in methanol (0.5 mL) was treated with NaOMe (0.5 N, 0.25 mL) and warmed to 60° C. for 25 min. the reaction was diluted, quenched with TFA, concentrated and subjected to flash chromatography to provide the title compound (19 mg) as a white solid.

LC-MS $R_{rt}$=1.57 min, (M+H$^+$) 186.00

$^1$H NMR (500 MHz, CDCl3) 9.30 (br s, 1H), 8.86 (s, 1H), 7.33 (dd, 1H), 6.98 (dd, 1H) 6.79 (dd, 1H), 3.06 (m, 2H), 2.70 (m, 2H), 2.13 (q, 2H)

Example 2

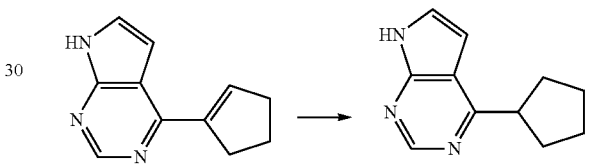

4-cyclopentyl-7H-pyrrolo[2,3-d]pyrimidine (Compound 3)

A mixture of 4-cyclopentenyl-7H-pyrrolo[2,3-d]pyrimidine (11 mg, 0.060 mmol) and Pd-C (10% on carbon, 22 mg) in EtOAc (1 mL) was stirred under $H_2$ atmosphere (balloon) for 5 h. The mixture was filtered and concentrated to provide the title compound (10 mg) as a white solid.

LC-MS $R_{rt}$=1.37 min, (M+H$^+$) 188.10

$^1$H NMR (500 MHz, CDCl3) 9.00 (br s, 1H), 8.80 (s, 1H), 7.24 (buried dd, 1H), 6.63 (dd, 1H), 3.56 (q, 2H), 2.13 (m, 2H), 2.05 (m, 2H), 1.92 (m, 2H), 1.75 (m, 2H)

The compounds in Examples 3-7 were made according to Scheme II.

Example 3

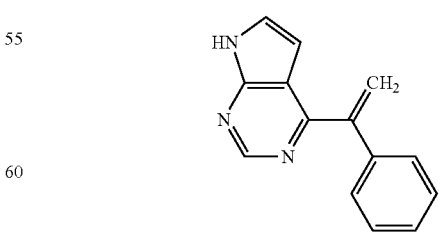

4-(1-phenylvinyl)-7H-pyrrolo[2,3-d]pyrimidine (Compound 8)

LC-MS $R_{rt}$=2 min, (M+H$^+$) 221

¹H NMR 500 MHz; DMSO-d6: 12.6(br m,1H), 8.85(s,1), 7.53(m,1H), 7.4(m,5H), 6.03(m,3H)

Example 4

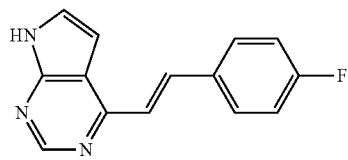 [SMILES: Fc1ccc(/C=C/c2ncnc3[nH]ccc23)cc1]

4-(4-fluorostyryl)-7H-pyrrolo[2,3-d]pyrimidine (Compound 5)

LC-MS $R_{tt}$=2 min, (M+H⁺) 239

¹H NMR: 500 MHz; DMSO-d6: 13.8(br m,1H), 8.93(s,1), 8.14(d,1H), 7.92(dd,2H), 7.83(m,1H), 7.71(d,1H), 7.35(dd,2H), 7.27(m,1H)

Example 5

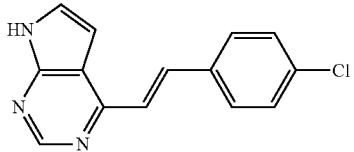 [SMILES: Clc1ccc(/C=C/c2ncnc3[nH]ccc23)cc1]

4-(4-chlorostyryl)-7H-pyrrolo[2,3-d]pyrimidine (Compound 6)

LC-MS $R_{tt}$=2.3 min, (M+H⁺) 255

¹H NMR: 500 MHz; DMSO-d6: 12.7(br m,1H), 8.90(s,1), 8.10(d,1H), 7.90(d,2H), 7.79(m,2H), 7.54(d,2H), 7.22(m,1H)

Example 6

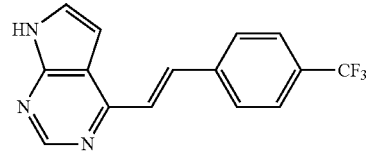 [SMILES: FC(F)(F)c1ccc(/C=C/c2ncnc3[nH]ccc23)cc1]

4-(4-(trifluoromethyl)styryl)-7H-pyrrolo[2,3-d]pyrimidine (Compound 7)

LC-MS $R_{tt}$=2.7 min, (M+H⁺) 289

¹H NMR: 500 MHz; DMSO-d6: 12.5(br m,1H), 8.88(s,1), 8.15(d,1H), 8.07(d,2H), 7.90(d,1H), 7.85(d,2H), 7.75(m,1H), 7.45(m,1H), 7.17(m,1H)

Example 7

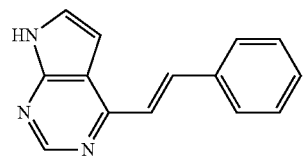 [SMILES: C(=C\c1ncnc2[nH]ccc12)/c1ccccc1]

4-styryl-7H-pyrrolo[2,3-d]pyrimidine (Compound 4)

LC-MS $R_{tt}$=2 min, (M+H⁺) 221

¹H NMR: 500 MHz; DMSO-d6: 12.8(br m,1H), 8.93(s,1), 8.14(d,2H), 7.85(d,2H), 7.83(m,1H), 7.75(d,1H), 7.51(d,2H), 7.47(m,1H), 7.28(m,1H)

Example 8

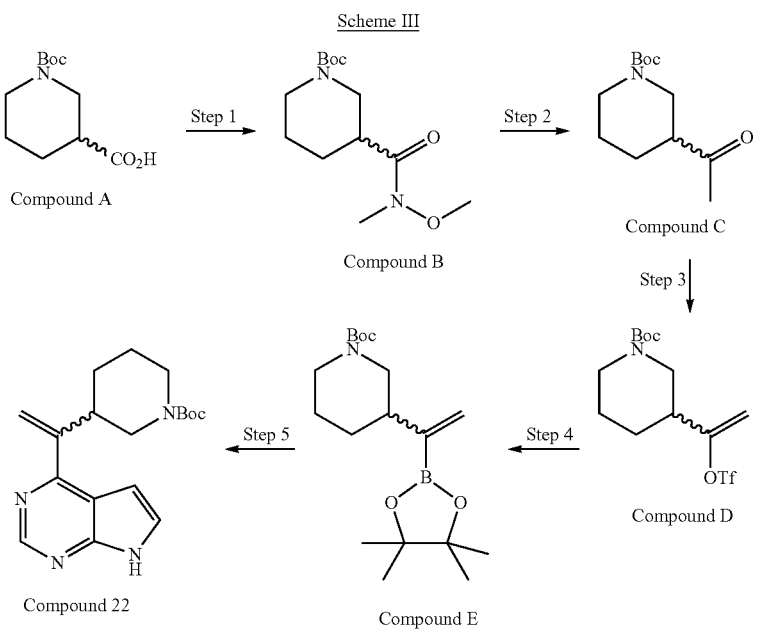

Scheme III

Step 1: Compound A (1-(tert Butoxycarbonyl)-3-piperidine carboxylic acid) (4.60 g, 20.0 mMol) was suspended in 40 ml of CH$_2$Cl$_2$. Added was EDCI (4.60 g, 24.0 mMol), followed by N,O-Dimethylamine (HCl) (2.34 g (24.0 mMol) and catalytic DMAP. The resulting mixture was allowed to stir at room temperature overnight. All volatiles were removed at reduced pressure. The residue was dissolved in saturated aqueous NaHCO$_3$ solution and EtOAc. The layers were separated and the organic was washed with brine, dried over MgSO$_4$, filtered and evaporated to dryness. No further purification, material used as is. Yield: 4.7 g, approximately 86%. H NMR (500 MHz, CDCl3) 3.73 (s, 3H), 3.18 (s, 3H), 2.87-2.81 (m, 4H), 1.94 (s, H), 1.73-1.65 (m, 4H), 1.49-1.46 (m, 9H).

Step 2: To a solution of compound B (4.7 g, 17.2 mMol) in 70 ml of THF at 0° C. (under N$_2$) was added a 3.0 M (11.5 ml, 34.5 mMol) solution of Methyl Magnesium Bromide in THF. After the addition was complete, the cooling bath was removed and the resulting mixture was allowed to rise to room temperature where it was allowed to stir overnight. The resulting mixture was quenched with a saturated aqueous KHSO$_4$ solution and diluted with EtOAc. The organic phase was washed with brine, dried over MgSO$_4$, filtered and evaporated to dryness. The crude residue was passed through a plug of silica gel and eluted with 5-20% EtOAc/Hexane. Yield: 2.37 g, approximately 60%. H NMR (500 MHz, CDCl3) 4.10 (d, J=12.0 Hz, H), 3.92 (s, H), 2.94 (dd, J=10.3, 13.3 Hz, H), 2.82-2.77 (m, H), 2.52-2.48 (m, H), 2.18 (s, 3H), 1.98 (dd, J=3.6, 12.9 Hz, H), 1.73-1.69 (m, H), 1.56-1.44 (m, 11H).

Step 3: Compound C (2.37 g, 10.4 mMol) was dissolved in 5.0 ml of THF and added (under N$_2$) to a solution of LiHMDS (13.0 ml, 13.0 mMol) at −78° C. (IPA-dry ice bath). After 30 min., added was 2-[N,N-bis(trifluoromethylsulfonyl) amino] pyridine (4.11 g, 11.5 mMol) and after 10 min. the cooling bath was removed. The resulting mixture gradually rose to room temperature where it was allowed to stir overnight. The resulting mixture was quenched with saturated aqueous KHSO$_4$ solution and diluted with EtOAc. The layers were separated and the organic was washed with brine, dried over MgSO$_4$, filtered and evaporated to dryness. The crude was passed through a plug of silica gel and eluted with 10% EtOAc / Hexane. Yield: 2.93 g, approximately 79%. H NMR (500 MHz, CDCl3) 5.19 (d, J=4.1 Hz, H), 5.01 (dd, J=1.0, 4.1 Hz, H), 4.14-4.11 (m, H), 2.84 (dd, J=9.7, 13.2 Hz, 3H), 2.41 (s, H), 2.04-2.00 (m, H), 1.72 (t, J=3.4 Hz, H), 1.52-1.46 (m, 11H).

Step 4: Compound D (2.93 g, 8.2 mMol) was dissolved in 30 ml of toluene. Added was Bis(Pinacoloto)diboron (2.07 g, 8.2 mMol) followed by Triphenyl phosphine (117.3 mg, 0.44 mMol) and Potassium phenoxide (1.48 g, 11.2 mMol). The RM was degassed with Ar for 5 min. Added was trans-Dichlorobis (triphenylphosphine)palladium (II) (157.0 mg, 0.22 mMol) and the resulting mixture was allowed stir at 55° C. for 3 hours. The resulting mixture was allowed to cool to room temperature where it was stirred overnight. The resulting mixture was diluted with saturated aqueous NaHCO$_3$ solution and EtOAc. The layers were separated and the organic was washed with brine, dried over MgSO$_4$, filtered and evaporated to dryness. The crude was passed through a plug of silica gel eluting with 5-15 % EtOAc/Hexane. Phenol was still present, so material was dissolved in Et$_2$O and washed with 1N NaOH solution. The organic phase was dried over MgSO$_4$, filtered and evaporated to dryness. Yield: 2.01 g, approximately 73%. H NMR (500 MHz, CDCl3) 5.83 (d, J=2.6 Hz, H), 5.65 (s, H), 4.07 (dd, J=1.6, 12.8 Hz, 2H), 2.64-2.58 (m, 2H), 2.26 (t, J=11.2 Hz, H), 1.82-1.79 (m, H), 1.67-1.64 (m, H), 1.50 (t, J=3.7 Hz, 11H), 1.29-1.19 (m, 12H).

Step 5: Compound E (45.7 mg, 0.14 mMol) was dissolved in 1.0 ml of DME. Added was 4-Chloro-7H-pyrrolo[2,3-d] pyrimidine (20.8 mg, 0.14 mMol) followed by a 2.0 M solution of Na$_2$CO$_3$ (200 uL, 0.4 mMol). The resulting mixture was degassed with Ar for 5 minutes and added was catalytic tetrakis triphenylphosphine palladium (0). The resulting mixture was warmed to 160° C. via microwave irradiation. After 10 minutes, the resulting mixture was cooled to room temperature. The resulting mixture was diluted with H$_2$O and EtOAc. The layers were separated and the organic washed with brine, dried over MgSO$_4$, filtered and evaporated to dryness. The crude residue was chromatographed on a plug of silica gel and eluted with 10-30% EtOAc/Hexane. Yield: 7.1 mg of Compound 22.

Example 9

Scheme IV

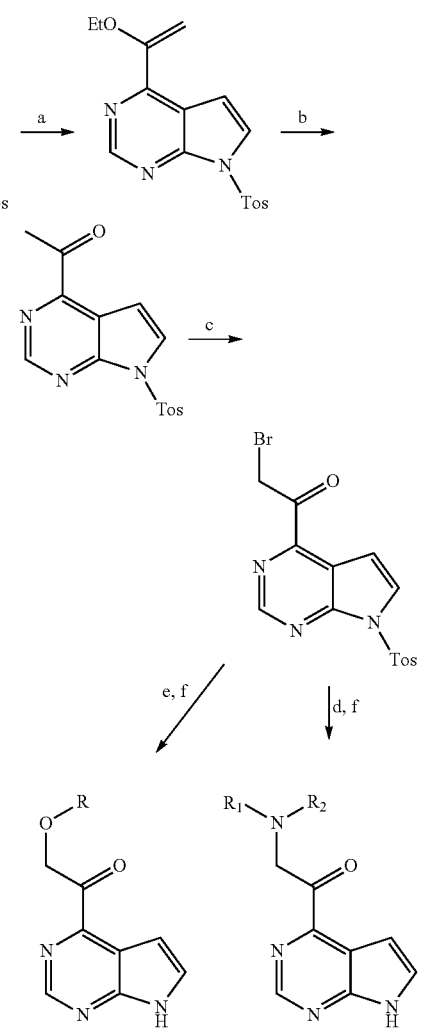

(a) tri-n-butyl(1-ethoxyvinyl) tin, Pd(PPh$_3$)$_2$Cl$_2$, toluene, 90° C.
(b) 6N HCl, MeOH, THF
(c) HBr, HOAc
(d) HNR$_1$R$_2$, Et$_3$N
(e) NaOR or HOR, Et$_3$N
(f) LiOH, or NaOMe

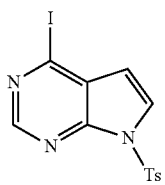 [SMILES: Cc1ccc(S(=O)(=O)n2ccc3c(I)ncnc32)cc1]

4-Iodo-7-(toluene-4-sulfonyl)-7H-pyrrolo[2,3-d]pyrimidine: [5 g. 16.2 mmol] of 4-Chloro-7-(toluene-4-sulfonyl)-7H-pyrrolo[2,3-d]pyrimidine (as described in Example 1) was added in small portions, to 100 mL of cold stirring 47% stabilized hydriodic acid at 0° C. and stirred for one hour cold; the temperature was then allowed to warm to ambient temperature and stirred an additional 5 hrs. The reaction mixture was diluted with water and the solid was isolated via suction filtration, the solid being washed with additional water. The crude solid was dissolved in dichloromethane and washed with saturated sodium hydrogen carbonate solution twice, brined, dried (Na$_2$SO$_4$) and the solvent was removed under reduced pressure and triturated with a 2:1 mixture of hexanes/MTBE to yield 5.7 g of a white material (88%). $^1$H NMR: 500 Mhz in CDCL3 δ8.61(s,1H), 8.06(d,2H J=8.5 Hz), 7.75(d,1H J=4.1 Hz), 7.32(d,2H J=8.5 Hz), 6.45(d,1H J=4.1 Hz), 2.4(s, 3H).

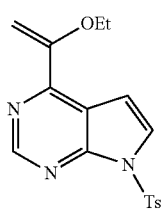 [SMILES: C=C(OCC)c1ncnc2c1ccn2S(=O)(=O)c1ccc(C)cc1]

Step a: 4-(1-Ethoxy-vinyl)-7-(toluene-4-sulfonyl)-7H-pyrrolo[2,3-d]pyriniidine: [10 g, 25 mmol] of 4-Iodo-7-(toluene-4-sulfonyl)-7H-pyrrolo[2,3-d]pyrimidine (as described above) was dissolved/suspended in 200 mL of dry toluene along with [2.0 g, 2.85 mmol] of palladium (II) bis-triphenylphosphine dichloride. The mixture was purged with nitrogen gas for ~5 minutes before mixture was heated to 90° C. in an oil bath under an atmosphere of nitrogen gas. Added slowly dropwise over 2 hours, was [12.66 mL, 13.54 g, 37.5 mmol] of tri-n-butyl(1-ethoxyvinyl) tin in 100 mL of dry toluene. After completing the addition, the mixture was heated for an additional 6 hours under nitrogen. The reaction was cooled to ambient temperature and the solvent was removed under reduced pressure until the remaining volume was ⅕ the original. Added to this slurry was 160 mL of petroleum ether and the mixture was stirred for 1 hour, the solid being isolated via suction filtration and washed with petroleum ether. The damp solid was slurried in acetonitrile, stirred for one hour and the solid re-isolated via suction filtration and airdried. The resulting pale yellow solid, 7.2 g representing an 82% yield was utilized without further treatment. $^1$H NMR: 500 Mhz in CDCL3 δ8.9(s,1H), 8.07(d, 2H, J=8.5 Hz), 7.7(d, 1H, J=4.1 Hz), 7.28(d,2H, J=8.5 Hz), 7.04 (d,1H, J=4.1 Hz), 5.7(d,1H, J=2 Hz), 4.58(d,1H,J=2 Hz), 4.0(quart,2H), 2.4(s,3H), 1.5(t,3H).

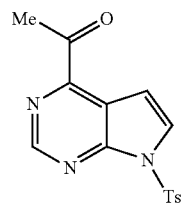 [SMILES: CC(=O)c1ncnc2c1ccn2S(=O)(=O)c1ccc(C)cc1]

Step b: 1-[7-(Toluene-4-sulfonyl)-7H-pyrrolo[2,3-d]pyrimidin-4-yl]-ethanone: [7.25 g, 21.12 mmol] of 4-(1-Ethoxy-vinyl)-7-(toluene-4-sulfonyl)-7H-pyrrolo[2,3-d]pyrimidine was dissolved in 50 mL each of methanol and THF and stirred with 10 mL of 6N HCL for 4.0 hours at ambient temperature. The solvents were removed under reduced pressure and the residue was partitioned between dichloromethane and saturated sodium hydrogen carbonate solution. The organic fraction was brined and dried with anhydrous sodium sulphate and the solvent was removed under reduced pressure. The crude material was triturated with a mixture of MTBE and petroleum ether (1:4) for several hours and the solid finally isolated via suction filtration and air dried. The 5.95 g of pale yellow material, representing a 89% yield was used without further purification. $^1$H NMR: 500 Mhz CDCL3 δ9.0(s,1H), 8.08(d,2H, J=8.4 Hz), 7.87(d, 1H, J=4.1 Hz), 7.3(m,3H), 2.8(s,3H), 2.4(s,3H).

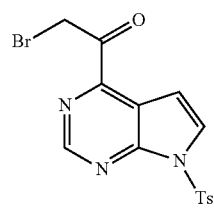 [SMILES: Cc1ccc(S(=O)(=O)n2ccc3c(C(=O)CBr)ncnc32)cc1]

Step c: 2-Bromo-1-[7-(toluene-4-sulfonyl)-7H-pyrrolo[2,3-d]pyriridin-4-yl]-ethanone: [5.95 g, 18.88 mmol] of 1-[7-(Toluene-4-sulfonyl)-7H-pyrrolo[2,3-d]pyrimidin-4-yl]-ethanone was dissolved/suspended in 90 mL of glacial acetic acid and [7.53 mL, 10.197 g, 37.76 mmol] of 30% hydrogen bromide in acetic acid. Added dropwise to this stirring mixture at ambient temperature, was [0.970 mL, 3.02 g, 18.88 mmol] of bromine in 10 mL of glacial acetic acid over 1.0 hour. The reaction was stirred an additional 4.0 hours at ambient temperature during which time a yellow precipitate forms. The solvent was removed under reduced pressure and the residue was partitioned between dichloromethane and sat'ed sodium hydrogen carbonate solution. The organic phase was washed with water, brine, and dried with anhydrous sodium sulphate and the solvent was removed under reduce pressure. The crude solid was triturated/stirred with MTBE overnight and the solid isolated via suction filtration and airdried to yield 4.2 g of pale yellow solid, a 56.6% yield. $^1$H NMR: 500 Mhz in CDCL3 δ9.1(s,1H), 8.09(d,2H, J=8.5 Hz), 7.93(d,1H, J=4.0 Hz), 7.33(d,2H, J=8.5 Hz). 7.29(d,1H, J=4.0 Hz), 4.83(s,2H), 2.4(s,3H).

Steps d, e: Conversion of the bromide may be accomplished upon nucleophilic displacement with primary or secondary amnines (i.e., step d) or upon treatment with an alcohol (i.e., step e) under basic conditions.

Step f: The compound is deprotected as described for Compound 1.

Example 10

Scheme V

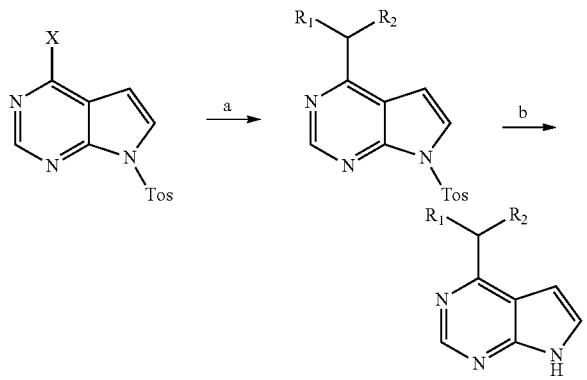

(a) Alkylzinc halide, THF, r.t.-100 C.
(b) LiOH/THF or NaOMe/MeOH

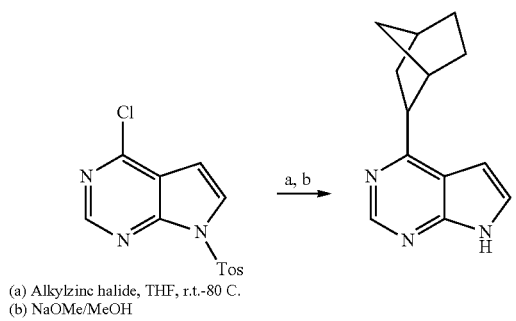

(a) Alkylzinc halide, THF, r.t.-80 C.
(b) NaOMe/MeOH

Steps a,b: 4-Bicyclo[2.2.1]hept-2-yl-7H-pyrrolo[2,3-d]pyrimidine: To a solution of N-tosyl-4-chlorodeazapurine (40 mg, 0.13 mmol) in anhydrous THF (0.5 mL) was added an appropriate alkylzinc halide (e.g., exo-2-norbornylzinc bromide [0.40 mL, 0.5 M]) and the mixture is stirred overnight at room temperature. Then the mixture is heated to 80° C. for an additional 1.5 h and cooled to room temperature. The reaction mixture is treated with NaOMe (200 uL, 0.5 M) in MeOH at 50° C. for 1.5 h before work up. Rochelle's salt is added and the mixture is extracted repeatedly with EtOAc. The organic layer is filtered and concentrated. The crude residue is purified by HPLC to provide the Compound 26. LC-MS: RT=1.86, (M+H)=214.2; $^1$H NMR (DMSO) 12.42 (m, 2H), 8.78 (s, 1H), 8.74 (s, 1H), 7.62 (br s, 2H), 6.82 (s, 1H), 6.77 (s, 1H), 3.76 (m, 1H), 3.31 (s, 1H), 2.75 (m, 1H), 2.46 (m, 1H), 2.37 (m, 2H), 2.14 (m, 2H), 1.90 (m, 1H), 1.72 (m, 1H), 1.67 (d, 2H), 1.59 (m, 2H), 1.55-1.42 (complex m, 3H), 1.33 (m, 2H), 1.23 (m, 1H), 1.17 (d, 1H), 0.99 (m, 1H).

Compounds 23, 24, 25, 27, 28, 29, 30 and 31 were prepared by the method described above.

Table 4 below depicts exemplary $^1$H-NMR data (NMR) and liquid chromatographic mass spectral data, reported as mass plus proton (M+H), as determined by electrospray, and retention time (RT) for certain compounds of the present invention, wherein compound numbers in Table 4 correspond to the compounds depicted in Table 3 (empty cells indicate that the test was not performed):

TABLE 4

| Cmpd # | M + H$^+$ | LC-MS R$_t$ | $^1$H NMR |
|---|---|---|---|
| 2 | Lot 1: 200.00 | Lot 1: 1.93 | Lot 1: (500 MHz, CDCl3) 8.92 (br s, 1H), 8.81 (s, 1H), 7.26 (burried dd, 1H), 6.86 (m, 1H), 6.72 (dd, 1H), 2.70 (m, 2H), 2.34 (m, 2H), 1.84 (m, 2H), 1.76 (m, 2H) |
| 9 | 301.00 | 2.05 | (CDCl3) 10.07 (br s, 1H), 8.86 (s, 1H), 7.35 (d, 1H), 6.83 (d, 1H), 6.73 (br s, 1H), 4.24 (br s, 2H), 3.71 (br s, 2H), 2.86 (br s, 2H), 1.52 (s, 9H) |
| 10 | | | (d4-methanol) 8.71 (s, 1H), 7.52 (d, 1H), 6.86 (m, 1H), 6.84 (d, 1H), 4.01 (br s, 2H), 3.54 (dd, 2H), 3.08 (br s, 2H) |
| 11 | 213.80 | 2.40 | (500 MHz, CDCl3) 9.24 (s, 1H), 7.7 (brs, 1H), 7.56 (s, 1H), 7.02 (d, 1H), 6.93 (br s, 1H), 3.68 (m, 2H), 2.62 (m, 2H), 2.28 (m, 1H), 2.16 (m, 1H), 2.03 (m, 1H), 1.94 (m, 1H), 1.29 (d, 3H) |
| 12 | 228.19 | 2.17 | (500 MHz, CD3OD) 8.90 (s, 1H), 7.81 (d, 1H), 6.95 (d, 1H), 5.83 (br s, 2H), 2.79 (m, 1H), 1.85 (complex m, 4H), 1.75 (br d, 1H), 1.47-1.24 (complex m, 5H) |
| 13 | 218.00 | 1.50 | 500 Mhz; DMSO-d6: 12.1 (br s, 1H), 8.7 (s, 1H), 7.5 (s, 1H), 7.0 (s, 1H), 6.73 (s, 1H), 3.45 (s, 2H), 2.9 (s, 4H) |
| 14 | 146.00 | 0.60 | (CDCl3) 10.70 (br s, 1H), 8.89 (s, 1H), 7.39 (d, 1H), 7.15 (dd, 1H), 6.73 (d, 1H), 6.66 (dd, 1H), 5.82 (dd, 1H) |
| 15 | 242.90 | 0.52 | |
| 16 | 310.90 | 1.61 | |
| 17 | 268.20 | 0.60 | (d4-methanol) 8.76 (s, 1H), 7.61 (d, 1), 6.93 (d, 1H), 6.90 and 6.86 (2m, 1H), 4.40 and 4.34 (2m, 2H), 4.01 and 3.97 (2s, 2H), 3.90 and 3.78 (2t, 2H), 2.94 (m, 2H) |
| 18 | 214.23 | 1.97 | (500 MHz, CD3OD) 8.81 (s, 1H), 7.66 (d, 1H), 6.85 (d, 1H), 5.78 and 5.77 (two s, 2H), 1.94 (m, 2H), 1.78 (m, 2H), 1.70 (m, 2H), 1.50 (m, 2H) ppm. |

TABLE 4-continued

| Cmpd # | M + H+ | LC-MS R$_t$ | $^1$H NMR |
|---|---|---|---|
| 19 | 214.21 | 1.75 | (500 MHz, CD3OD) 8.86 (s, 1H), 7.83 (d, 1H), 7.08 (d, 1H), 7.05 (m, 1H), 3.16 (m, 1H), 2.99 (m, 1H), 2.33 (m, 1H), 2.20 (m, 1H), 1.23 (d, 3H), 1.18 (d, 3H) ppm. |
| 20 | 214.20 | 2.60 | 1H NMR (500 MHz, CD3OD) 8.86 (s, 1H), 7.84 (m, 1H), 7.00 (m, 2H), 2.88 (m, 2H), 2.58 (m, 2H), 1.97 (m, 2H), 1.81 (m, 2H), 1.72 (m, 2H). |
| 21 | 211.90 | 1.60 | 500 MHz, CDCl3: 12.3.0 (br m, 1H), 9.0 (s, 1H), 7.63 (s, 1H), 7.58 (s, 1H), 6.93 (s, 1H), 3.75 (s, 1H), 3.30 (s, 1H), 1.97(m, 2H), 1.74 (d, 1H), 1.45 (d, 1H), 1.33 (m, 1H), 1.22 (m, 1H) |
| 22 | 328.90 | 2.46 | 500 Mhz, CDCl3 10.16 (s, br, 1H), 8.87 (s, 1H), 7.34 (s, 1H), 6.67 (s, 1H), 5.59 (s, 1H), 4.11 (d, br, 2H), 3.18 (m, 1H), 2.79 (t, 2H), 2.00 (m, 1H), 1.71 (m, 2H), 1.64-1.48 (m, 2H), 1.43 (s, 9H). |
| 23 | 224.20 | 1.91 | |
| 24 | 220.20 | 1.52 | 12.47 (br s, 1H), 8.79 (s, 1H), 7.65 (s, 1H), 6.81 (s, 1H), 3.55 (s, 3H), 3.39 (q, 1H), 3.16 (m, 2H), 1.15 (d, 3H) |
| 25 | 176.20 | 1.65 | |
| 27 | 216.20 | 2.04 | |
| 28 | 201.20 | 1.48 | |
| 29 | 234.20 | 1.52 | |
| 30 | 243.20 | 1.91 | |
| 31 | 190.20 | 1.91 | |

Example 11

JAK3 Inhibition Assay

Compounds were screened for their ability to inhibit JAK using the wn below. Reactions were carried out in a kinase buffer containing 100 mM HEPES (pH 7.4), 1 mM DTT, 10 mM MgCl$_2$, 25 mM NaCl, and 0.01% BSA.

Substrate concentrations in the assay were 5 μM ATP (200 uCi/μmole ATP) 1 μM poly(Glu)$_4$Tyr. Reactions were carried out at 25° C. and 1 nM JAK3.

To each well of a 96 well polycarbonate plate was added 1.5 μl of a JAK3 inhibitor along with 50 μl of kinase buffer containing 2 μM poly(Glu)$_4$Tyr and 10 μM ATP. This was then mixed and 50 μl of kinase buffer 2 nM JAK3 enzyme was added to start the reaction. After 20 minutes at room temperature (25C), the reaction was stopped with 50 μl of 20% trichloroacetic acid (TCA) that also contained 0.4 mM ATP. The entire contents of each well were then transferred to a 96 well glass fiber filter plate using a TomTek Cell Harvester. After washing, 60 μl of scintillation fluid was added and $^{33}$P incorporation detected on a Perkin Elmer TopCount.

Example 12

JAK2 Inhibition Assay

As described above in Example 11 except that JAK-2 enzyme is used, the final poly(Glu)$_4$Tyr concentration is 15 μM, and final ATP concentration is 12 μM.

Example 13

ROCK Inhibition Assays

Compounds are screened for their ability to inhibit ROCK I (AA 6-553) activity using a standard coupled enzyme system (Fox et al. Protein Sci. 7: 2249, 1998). Reactions are carried out in a solution containing 100 mM HEPES (pH 7.5), 10 mM MgCl$_2$, 25 mM NaCl, 2 mM DTT and 1.5% DMSO. Final substrate concentrations in the assay are 45 μM ATP (Sigma Chemicals, St Louis, Mo.) and 200 μM peptide (American Peptide, Sunnyvale, Calif.). Reactions are carried out at 30° C. and 45 nM ROCK I. Final concentrations of the components of the coupled enzyme system are 2.5 mM phosphoenolpyruvate, 350 μM NADH, 30 μg/ml pyruvate kinase and 10 μg/ml lactate dehydrogenase.

Compounds are screened for their ability to inhibit ROCK using a standard radioactive enzyme assay. Assays are carried out in a solution containing 100 mM HEPES (pH 7.5), 10 mM MgCl$_2$, 25 mM NaCl, 2 mM DTT and 1.5% DMSO. Final substrate concentrations in the assay are 13 μM [γ-$^{33}$P] ATP (25 mCi $^{33}$P ATP/mmol ATP, Perkin Elmer, Cambridge, Mass./Sigma Chemicals, St Louis, Mo.) and 27 μM Myelin Basic Protein (MBP). Final enzyme concentration in the assay is 5 nM ROCK. Assays are carried out at room temperature. 1.5 μl of DMSO stock containing serial dilutions of the compound of the present invention (concentrations ranging from 10 μM to 2.6 nM) is placed in a 96 well plate. 50 μl of Solution 1 (100 mM HEPES (pH 7.5), 10 mM MgCl$_2$, 26 mM [γ-$^{33}$P] ATP) is added to the plate. The reaction is initiated by addition of 50 μl of Solution 2 (100 mM HEPES (pH 7.5), 10 mM MgCl$_2$, 4 mM DTT, 54 mM MBP and 10 nM ROCK). After 2 hours the reaction is quenched with 50 μL of 30% trichloroacetic acid (TCA, Fisher) containing 9 mM ATP. Transfer of 140 μL of the quenched reaction to a glass fiber filter plate (Corning, Cat. No.3511) is followed by washing 3 times with 5% TCA. 50 μL of Optima Gold scintillation fluid (Perkin Elmer) is added and the plates are counted on a Top Count (Perkin Elmer). After removing mean background values for all of the data points the data is fit using Prism software to obtain a K$_i$(app).

Example 14

PKA Inhibition Assay

Compounds were screened for their ability to inhibit PKA using a standard coupled enzyme assay (Fox et al., *Protein Sci*, 1998, 7, 2249). Assays were carried out in a mixture of 100 mM HEPES (pH 7.5), 10 mM $MgCl_2$, 25 mM NaCl, 1 mM DTT and 3% DMSO. Final substrate concentrations in the assay were 50 µM ATP (Sigma Chemicals) and 80 µM peptide (Kemptide, American Peptide, Sunnyvale, Calif.). Assays were carried out at 30° C. and 18 nM PKA. Final concentrations of the components of the coupled enzyme system were 2.5 mM phosphoenolpyruvate, 300 µM NADH, 30 µg/ml pyruvate kinase and 10 µg/ml lactate dehydrogenase.

An assay stock buffer solution was prepared containing all of the reagents listed above, with the exception of ATP, and the test compound of the present invention. 55 µl of the stock solution was placed in a 96 well plate followed by addition of 2 µl of DMSO stock containing serial dilutions of the test compound of the present invention (typically starting from a final concentration of 5 µM). The plate was preincubated for 10 minutes at 30° C. and the reaction initiated by addition of 5 µl of ATP (final concentration 50 µM). Initial reaction rates were determined with a Molecular Devices SpectraMax Plus plate reader over a 15 minute time course. $IC_{50}$ and $K_i$ data were calculated from non-linear regression analysis using the Prism software package (GraphPad Prism version 3.0a for Macintosh, GraphPad Software, San Diego, Calif., USA).

Table 5 depicts enzyme inhibition data ($K_i$) for certain exemplary compounds. Compound numbers in Table 5 correspond to those compounds depicted in Table 3. In Table 5, "A" represents a $K_i$ of less than 0.5 µM, "B" represents a $K_i$ of between 0.5 and 5.0 µM, and "C" represents a $K_i$ of greater than 5.0 µM.

TABLE 5

| Cmpd # | JAK2 | JAK3 | PKA | ROCK |
|---|---|---|---|---|
| 1 | A | A | B | B |
| 2 | A | A | B | B |
| 3 | B | B | B | B |
| 4 | A | A | B | B |
| 5 | A | A | B | B |
| 6 | A | A | B | B |
| 7 | A | A | B | B |
| 8 | C | B | B | B |
| 9 | A | A | B | B |
| 10 | C | C | B | B |
| 11 | B | A | B | B |
| 12 | B | B | B | B |
| 13 | A | A | B | B |
| 14 | B | B | B | B |
| 15 | C | C | B | B |
| 16 | B | C | B | B |
| 17 | A | B | B | B |
| 18 | A | A | B | B |
| 19 | A | A | B | B |
| 20 | A | A | B | B |
| 21 | A | A | B | B |
| 22 | B | B | B | B |
| 23 | B | B | B | B |
| 24 | C | C | B | B |
| 25 | B | B | B | B |
| 26 | A | A | B | B |
| 27 | A | A | B | B |
| 28 | B | B | B | B |
| 29 | B | B | B | B |
| 30 | B | B | B | B |
| 31 | A | A | B | B |

We claim:
1. A compound of formula (I):

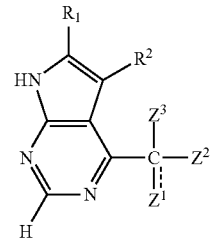

or a pharmaceutically acceptable salt thereof, wherein:
$R^1$ is H;
$R^2$ is H;
$Z^1$ and $Z^2$, together with the carbon atom to which they are attached, form ring Q;
$Z^3$ is H; or
$Z^1$, $Z^2$, and $Z^3$, together with the carbon atom to which they are attached, form a 6-14 membered saturated, partially saturated, or unsaturated bicyclic ring having 0-3 heteroatoms;
if the bond between $Z^1$ and C is a double bond, then $Z^3$ is absent;
Q is a 3-8 membered saturated or partially saturated monocyclic ring having 0-3 heteroatoms selected from nitrogen, oxygen, or sulfur, wherein said Q is optionally and independently fused to $Q^1$ or $Q^2$; or to both $Q^1$ and $Q^2$; wherein said Q is optionally substituted with 0-4 $J^Q$ groups;
$Q^1$ is a 3-8 membered saturated, partially saturated, or unsaturated monocyclic ring having 0-3 heteroatoms selected from nitrogen, oxygen, or sulfur, wherein said $Q^1$ group is optionally substituted with 0-4 $J^Q$ groups;
$Q^2$ is a 3-8 membered saturated, partially saturated, or unsaturated monocyclic ring having 0-3 heteroatoms selected from nitrogen, oxygen, or sulfur wherein said $Q^2$ group is optionally substituted with 0-4 $J^Q$ groups;
R is H, optionally substituted $C_{1-6}$ aliphatic, $C_{3-10}$ cycloaliphatic, $C_{6-10}$ aryl, 5-14 membered heteroaryl, or 5-14 membered heterocyclyl; or two R groups, on the same substituent or different substituents, together with the atom(s) to which each R group is bound, form an optionally substituted 3-14 membered saturated, partially unsaturated, or fully unsaturated monocyclic, bicyclic, or tricyclic ring having 0-4 heteroatoms independently selected from nitrogen, oxygen, or sulfur wherein each R is optionally substituted with 0-10 $J^R$ groups;
each $J^Q$ substituent on an unsaturated carbon atom is independently selected from hydrogen, —$OCF_3$, $C_{1-6}$haloalkyl, $N(R)_2$, OR, halogen, Y, —$(V)_n$—CN, —$(V)_n$—$NO_2$, —$(V)_n$—OH, —$(V)_n$—($C_{1-6}$aliphatic), —($C_{3-10}$cycloaliphatic)-C(O)R, —($C_{3-10}$cycloaliphatic)-($C_{3-12}$heterocyclyl); —$(V)_n$—($C_{3-12}$heterocyclyl), —$(V)_n$—($C_{6-10}$aryl), —$(V)_n$-(5-10 membered heteroaryl), —$(V)_n$—($C_{3-10}$cycloaliphatic); wherein each $J^Q$ is optionally substituted with up to 10 $J^R$ groups;
each $J^Q$ substituent on a saturated carbon atom is selected from those listed above for an unsaturated carbon and also the following: =O, =$NN(R^a)_2$, =$NNHC(O)R^a$, =$NNHCO_2(C_{1-4}alkyl)$, =$NNHSO_2(C_{1-4}alkyl)$, and =$NR^a$ wherein each $J^Q$ is optionally substituted with up to 10 $J^R$ groups;
each $J^Q$ substituent on an unsaturated carbon atom is independently selected from hydrogen, Y, —$(V)_n$—CN, —$(V)_n$—$NO_2$, —$(V)_n$—OH, —$(V)_n$—($C_{1-6}$aliphatic), —($C_{3-10}$cycloaliphatic)-C(O)R, —($C_{3-10}$cycloaliphatic)-(C$_{3-12}$heterocyclyl); —(V)$_n$ —(C$_{3-12}$heterocyclyl), —(V)$_n$—(C$_{6-10}$aryl), —(V)$_n$-(5-10 membered heteroaryl), —(V)$_n$—(C$_{3-10}$cycloaliphatic); wherein each J$^Q$ is optionally substituted with up to 10 J$^R$ groups;

J$^R$ is selected from halogen, —N(R$^b$)$_2$, SR$^b$, OR$^b$, oxo, C$_{1-4}$haloalkoxy, C$_{1-4}$haloalkyl, L, -(L)$_n$-(C$_{1-6}$alkyl), -(L)$_n$-(C$_{3-12}$heterocyclyl), -(L)$_n$-(C$_{6-10}$aryl), -(L)$_n$-(5-10 membered heteroaryl), -(L)$_n$-(C$_{3-10}$cycloalipahtic), -(L)$_n$-NO$_2$, -(L)$_n$-CN, -(L)$_n$-OH, —CO$_2$R$^b$, —COR$^b$, —OC(O)R$^b$, —NHC(O)R$^b$;

L is C$_{1-10}$alkyl wherein up to three methylene units are replaced by —NR$^b$—, —O—, —S—, —CO$_2$—, —OC(O)—, —C(O)CO—, —C(O)—, —C(O)NR$^b$—, —C(=N—CN), —NR$^b$CO—, —NR$^b$C(O)O—, —SO$_2$NR$^b$—, —NR$^b$SO$_2$—, —NR$^b$C(O)NR—, —OC(O)NR$^b$—, —NR$^b$SO$_2$NR$^b$—, —SO—, or —SO$_2$—;

V is C$_{1-10}$aliphatic wherein up to three methylene units are replaced by G$^V$, wherein G$^V$ is selected from —NR—, —O—, —S—, —CO$_2$—, —OC(O)—, —C(O)CO—, —C(O)—, —C(O)NR—, —C(=N—CN), —NRCO—, —NRC(O)O—, —SO$_2$NR—, —NRSO$_2$—, —NRC(O)NR—, —OC(O)NR—, —NRSO$_2$NR—, —SO—, or —SO$_2$—;

Y is C$_{1-10}$aliphatic, wherein up to three methylene units are replaced by G$^Y$ wherein G$^Y$ is selected from —NR—, —O—, —S—, —CO$_2$—, —OC(O)—, —C(O)CO—, —C(O)—, —C(O)NR—, —C(=N—CN), —NRCO—, —NRC(O)O—, —SO$_2$NR—, —NRSO$_2$—, —NRC(O)NR—, —OC(O)NR—, —NRSO$_2$NR—, —SO—, or —SO$_2$—;

R$^a$ is hydrogen or C$_{1-6}$ aliphatic group optionally substituted with 0-3 J$^R$ groups;

R$^b$ is hydrogen or an unsubstituted C$_{1-6}$ aliphatic group; n is 0 or 1.

2. The compound according to claim 1, wherein Z$^1$ and Z$^2$, together with the carbon atom to which they are attached, form a compound as shown in Formula IV:

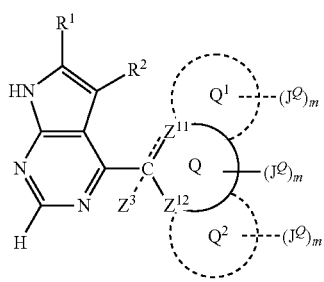

IV wherein
Z$^{11}$ is selected from C, N, O, or S;
Z$^{12}$ is selected from C, N, O, or S;
Q is a 3-8 membered saturated or partially saturated monocyclic ring, optionally fused to Q$^1$ or Q$^2$;
Q$^1$ and Q$^2$ are each independently a 3-8 membered saturated, unsaturated, or partially saturated monocyclic rings;
Q, Q$^1$ and Q$^2$ each independently contain up to three heteroatoms selected from O, N, or S;
m is 0-4; and is independently selected for Q, Q$^1$ and Q$^2$; and
Z$^3$ is H; or if the bond between C and Z$^{11}$ is a double bond, then Z$^3$ is absent.

3. The compound according to claim 1, wherein Q or Q-Q$^1$ is selected from:

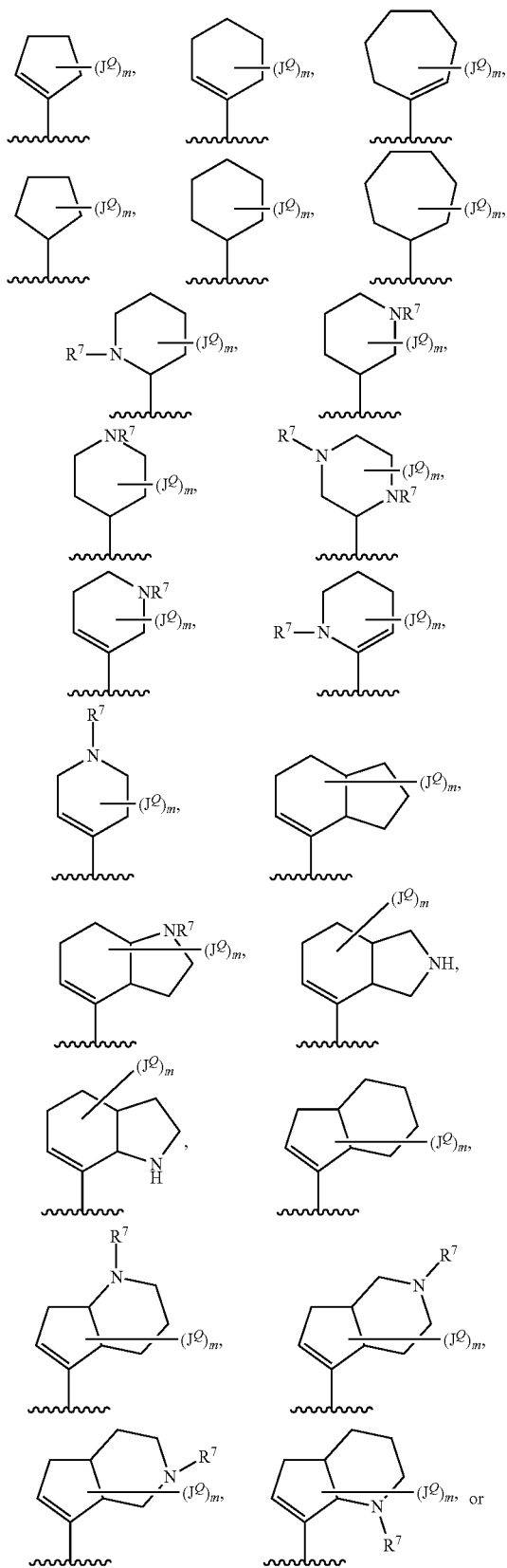

-continued

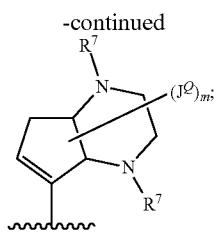

wherein
both R[7] and J[Q] are each independently selected from hydrogen, Y, —(V)$_n$—CN, —(V)$_n$—NO$_2$, —(V)$_n$—OH, —(V)$_n$—(C$_{1-6}$aliphatic), —(V)$_n$—(C$_{3-12}$heterocyclyl), —(V)$_n$—(C$_{6-10}$aryl), —(V)$_n$-(5-10 membered heteroaryl), —(V)$_n$ —(C$_{3-10}$cycloaliphatic) and —(C$_{3-10}$cycloaliphatic)-(C$_{3-12}$heterocyclyl);
each, m is independently 0-2; and
each R[7] and J[Q] is optionally and independently substituted with 0-10 J[R] groups.

4. The compound according to claim 1 having formula VII:

Formula VII

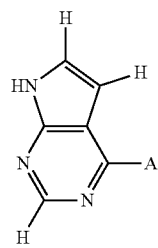

wherein A is selected from:

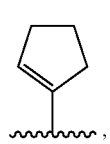 , 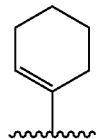 , 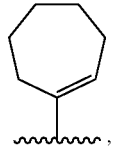 ,

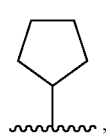 , 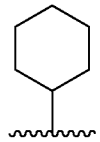 , 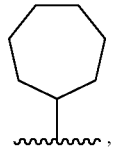 ,

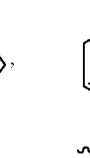 ,  ,

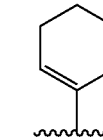 , 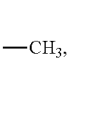 ,

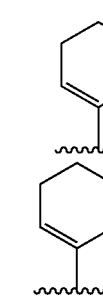 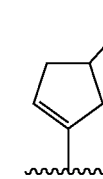 ,  ,

-continued

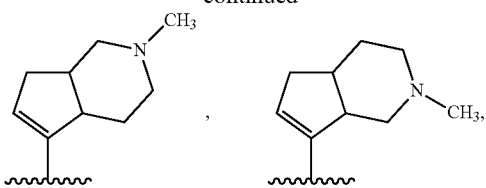

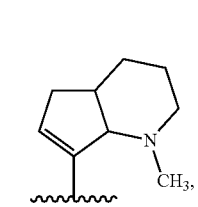 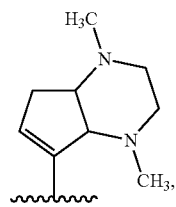

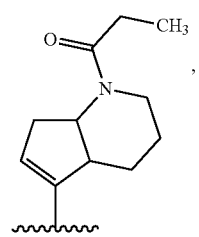 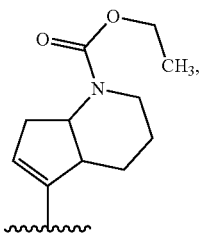

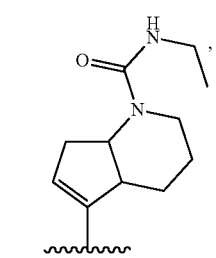 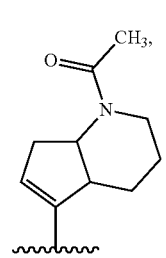

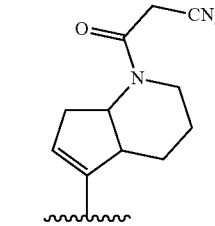 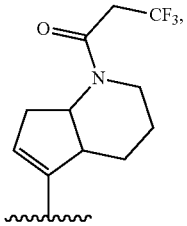

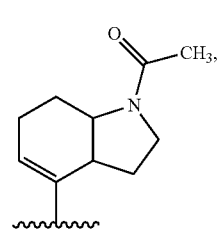 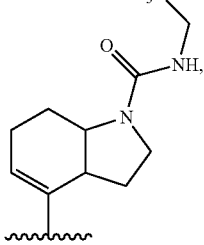

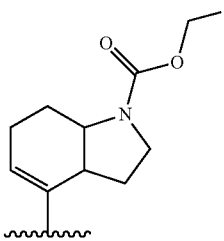 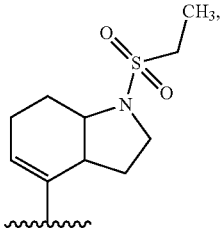

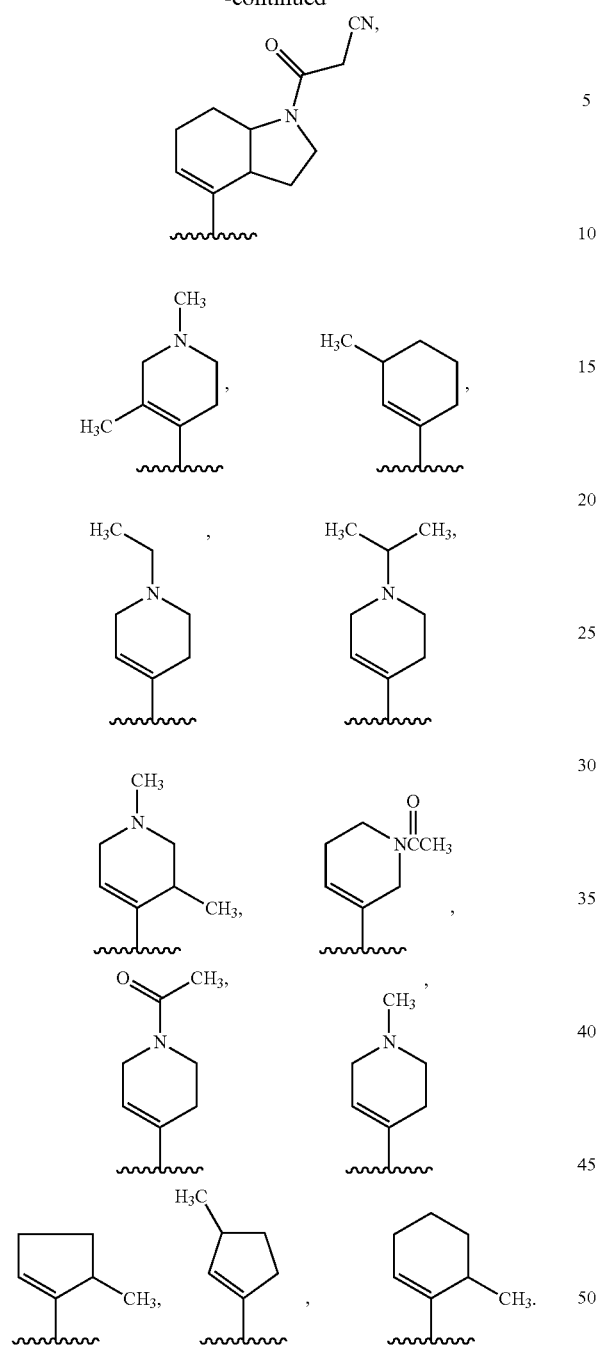
5. A compound selected from:
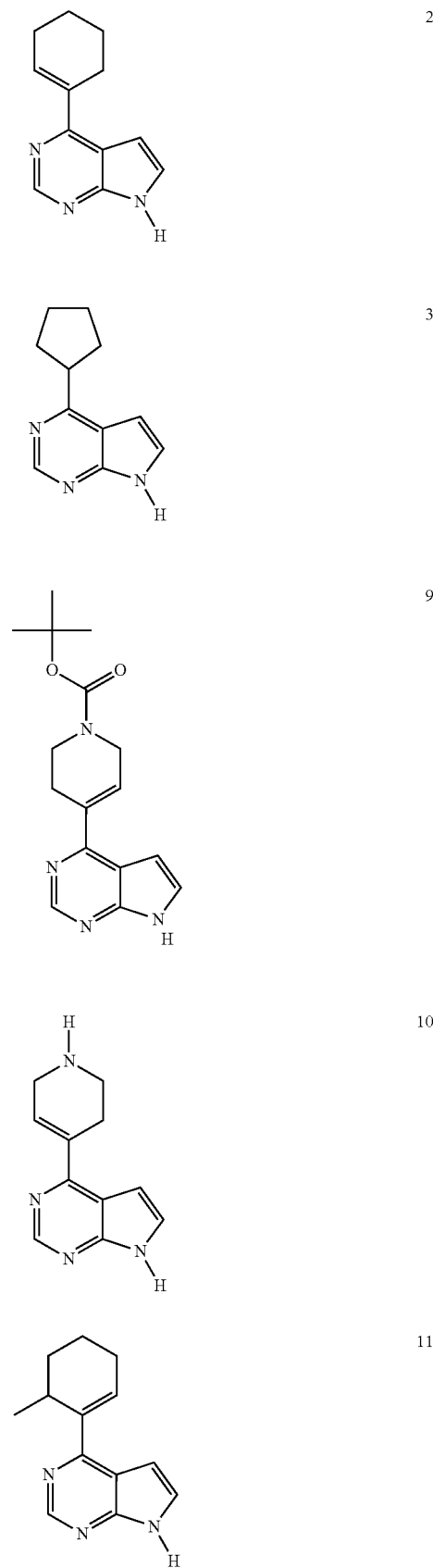

13 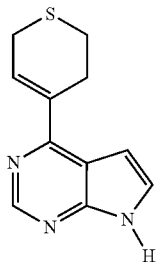

15 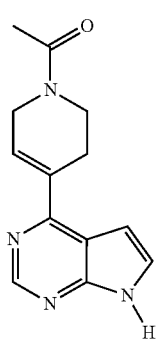

16 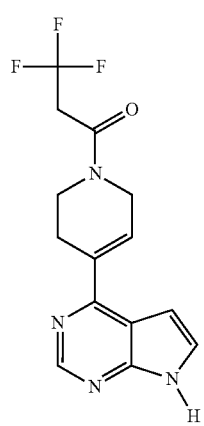 [SMILES: O=C(CC(F)(F)F)N1CC=C(c2ncnc3[nH]ccc23)CC1]

17 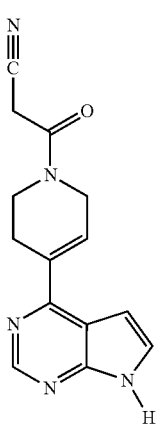

19 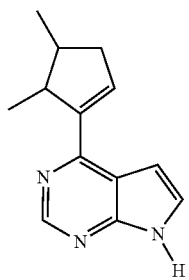 [SMILES: CC1CC=C(c2ncnc3[nH]ccc23)C1C]

20 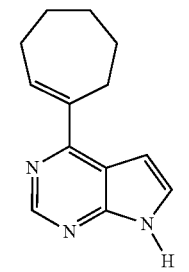 [SMILES: C1=C(c2ncnc3[nH]ccc23)CCCCC1]

21 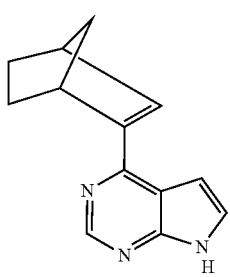

26 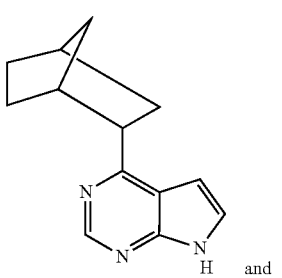 and

27 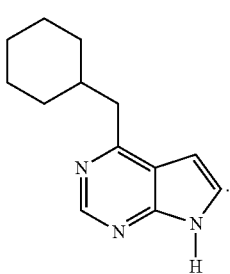 [SMILES: c1nc(CC2CCCCC2)c2cc[nH]c2n1]

6. The composition of claim 5, additionally comprising a therapeutic agent selected from a chemotherapeutic or antiproliferative agent, an anti-inflammatory agent, an immunomodulatory or immunosuppressive agent, a neurotrophic factor, an agent for treating cardiovascular disease, an agent for treating diabetes, or an agent for treating immunodeficiency disorders.

* * * * *